United States Patent
Sullenger et al.

(10) Patent No.: US 9,340,591 B2
(45) Date of Patent: May 17, 2016

(54) METHOD OF MODULATING THE ACTIVITY OF A NUCLEIC ACID MOLECULE

(75) Inventors: Bruce A. Sullenger, Durham, NC (US); Sabah Oney, Durham, NC (US); Tung Suet Ruby Lam, Durham, NC (US); Kam Leong, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

(21) Appl. No.: 12/588,016

(22) Filed: Sep. 30, 2009

(65) Prior Publication Data

US 2010/0184822 A1    Jul. 22, 2010

Related U.S. Application Data

(63) Continuation-in-part of application No. PCT/US2008/004119, filed on Mar. 31, 2008.

(60) Provisional application No. 60/920,807, filed on Mar. 30, 2007, provisional application No. 61/243,078, filed on Sep. 16, 2009.

(51) Int. Cl.
| | |
|---|---|
| *C12Q 1/68* | (2006.01) |
| *C07K 14/46* | (2006.01) |
| *A61K 31/00* | (2006.01) |
| *C12N 15/11* | (2006.01) |
| *G01N 33/53* | (2006.01) |
| *G01N 33/94* | (2006.01) |
| *A61K 38/00* | (2006.01) |

(52) U.S. Cl.
CPC .................. *C07K 14/46* (2013.01); *A61K 31/00* (2013.01); *C12N 15/111* (2013.01); *G01N 33/5308* (2013.01); *G01N 33/94* (2013.01); *A61K 38/00* (2013.01); *C12N 2310/16* (2013.01); *C12N 2320/50* (2013.01); *G01N 2500/00* (2013.01)

(58) Field of Classification Search
CPC . C12N 15/11; C12N 2310/16; C12N 2310/18
See application file for complete search history.

(56) References Cited

U.S. PATENT DOCUMENTS

| | | | | |
|---|---|---|---|---|
| 5,834,184 | A * | 11/1998 | Harada et al. | 435/6.12 |
| 7,300,922 | B2 * | 11/2007 | Sullenger et al. | 514/44 R |
| 7,304,041 | B2 * | 12/2007 | Rusconi | 514/44 R |
| 7,611,835 | B2 | 11/2009 | Kim et al. | |
| RE43,612 | E | 8/2012 | Anderson et al. | |
| 8,470,963 | B2 | 6/2013 | Koltermann | |
| 8,586,524 | B2 * | 11/2013 | Sullenger et al. | 514/1.1 |
| 2003/0083294 | A1 | 5/2003 | Sullenger et al. | |
| 2003/0143217 | A1 | 7/2003 | Baird et al. | |
| 2003/0180250 | A1 | 9/2003 | Chauhan et al. | |
| 2006/0040881 | A1 * | 2/2006 | Rusconi | 514/44 |
| 2008/0199485 | A1 | 8/2008 | Kundig et al. | |
| 2008/0267903 | A1 | 10/2008 | Uchegbu et al. | |
| 2009/0048193 | A1 * | 2/2009 | Rusconi et al. | 514/44 |
| 2009/0082250 | A1 | 3/2009 | Hart et al. | |
| 2009/0208501 | A1 | 8/2009 | Visintin et al. | |
| 2009/0298710 | A1 | 12/2009 | Farokhzad et al. | |
| 2010/0028402 | A1 | 2/2010 | Dobrovolskaia et al. | |
| 2010/0210746 | A1 | 8/2010 | Gustafson et al. | |
| 2010/0249217 | A1 * | 9/2010 | Sullenger et al. | 514/44 R |
| 2010/0285081 | A1 | 11/2010 | Chen et al. | |
| 2011/0118187 | A1 * | 5/2011 | Sullenger et al. | 514/13.8 |
| 2012/0128782 | A1 | 5/2012 | Green et al. | |
| 2012/0183564 | A1 | 7/2012 | Sullenger | |
| 2013/0266664 | A1 | 10/2013 | Yang et al. | |

FOREIGN PATENT DOCUMENTS

| | | | |
|---|---|---|---|
| WO | 02/19822 | A1 | 3/2002 |
| WO | 03/002592 | A1 | 1/2003 |
| WO | WO 2008/121354 | | 10/2008 |
| WO | WO 2010020008 | | 2/2010 |
| WO | WO 2013040552 | | 3/2013 |

OTHER PUBLICATIONS

Joachimi et al. JACS 2007 129, 3036-3037.*
John Chase Ann. Rev. Biochem. 1986 55: 103-36.*
Stephen Lippard Accounts of Chemical Research 11, 1978, 211-217.*
Eichhorn et al. Journal of the American Chemical Society 90:26, 1968, 7323-7328.*
International Search Report for PCT/US2008/004119 mailed Jun. 26, 2008.
Written Opinion for PCT/US2008/004119 mailed Jun. 26, 2008.
International Supplemental Search Report dated Jul. 11, 2011—International Appln. No. PCT/US2008/004119.
Astrid Joachimi et al., "A New Anticoagulant-Antidote Pair: Control of Thrombin Activity by Aptamers and Porphyrins", Journal of the American Chemical Society, vol. 129, No. 11, Mar. 1, 2007, pp. 3036-3037.
Z. Mérai et al., "Double-Stranded RNA Binding May Be a General Plant RNA Viral Strategy to Suppress RNA Silencing", Journal of Virology, vol. 80, No. 12, Jun. 15, 2006, pp. 5747-5756.
Z. Lichner et al., "Double-stranded RNA-binding proteins could suppress RNA interference-mediated antiviral defences", Journal of General Virology, vol. 84, No. 4, Apr. 1, 2003, pp. 975-980.
Rusconi C. P. et al., "Antidote-mediated control of an anticoagulant aptamer in vivo", Nature Biotechnology, Nature Publishing Group, New York, NY, US, vol. 22, No. 11, Nov. 1, 2004, pp. 1423-1428.
Rusconi C.P. et al., "RNA aptamers as reversible antagonists of coagulation factor IXa", Nature, Nature Publishing Group, Longon, GB, vol. 419, Sep. 5, 2002, pp. 90-94.
Que-Gewirth NS et al., "Gene therapy progress and prospects: RNA aptamers", Gene Therapy, MacMillan Press Ltd., Basingstoke, GB, vol. 14, No. 4, Feb. 1, 2007, pp. 283-291.

(Continued)

*Primary Examiner* — Brian Whiteman
(74) *Attorney, Agent, or Firm* — Andrus Intellectual Property Law, LLP

(57) ABSTRACT

The present invention relates, in general, to agents that modulate the pharmacological activity of nucleic acid molecules and, in particular, to agents that bind therapeutic or diagnostic nucleic acid molecules in a sequence independent manner and modulate (e.g., inhibit or reverse) their activity. The invention also relates to compositions comprising such agents and to methods of using same.

20 Claims, 18 Drawing Sheets

(56) References Cited

OTHER PUBLICATIONS

White R. R. et al., "Developing aptamers into therapeutics", Journal of Clinical Investigation, American Society for Clinical Investigation, US, vol. 106, No. 8, Oct. 1, 2000, pp. 929-934.

Sabah Oney et al., "Development of universal antidotes to control aptamer activity", Nature Medicine, vol. 15, No. 10, Oct. 1, 2009, pp. 1224-1229.

Chase et al, "Single-Stranded DNA Binding Proteins Required for DNA Replication", Ann. Rev. Biochem. 55:103-36 (1986).

Holl, et al., "Nucleic acid scavenging polymers inhibit extracellular DNA-mediated innate immune activation without inhibiting antiviral responses," (2013) *Plos One*, 8(7): 1-10.

Holl et al., "The nucleic acid scavenger polyamidoamine third-generation dendrimer inhibits fibroblast activation and granulation tissue contraction" (2014) *Plast Reconstr Surg* 134: 420e-33e.

Kotra et al., "Aminoglycosides: Perspectives on mechanisms of action and resistance and strategies to counter resistance," *Antimicrobial Agents and Chemotherapy* 44(12):3249-3256.

Lee et al., "Nucleic acid-binding polymers as anti-inflammatory agents," (2011) *Proc. Natl. Acad. Sci.* 108(34):14055-60.

Yu, P., "Nucleic Acid recognizing Toll-like receptors as therapeutic targets: a focus on autoimmunity and cancer", Journal of Receptor, (2009) *Ligand and Channel Research* 2:19-28.

Supplemental European Search Report dated Jun. 27, 2013 issued in connection with EP 10 81 7556 (9 pages).

Office Action dated Nov. 4, 2014 for U.S. Appl. No. 13/496,313 (9 pages).

Office Action dated Jun. 3, 2015 for U.S. Appl. No. 13/496,313 (10 pages).

\* cited by examiner

| ID | Protamine (ug) | Ch-9.3t (nM) | Time (min) | Clot Time (s) |
|---|---|---|---|---|
| 1 | 0 | 0 | 5 | 34.5 |
| 2 | 0 | 150 | 5 | 86.6 |
| 3 | 2.5 | 0 | 5 | 24 |
| 4 | 2.5 | 150 | 5 | 30.3 |
| 5 | 2.5 | 150 | 10 | 28.4 |
| 6 | 2.5 | 150 | 10 | 29.1 |
| 7 | 2.5 | 150 | 15 | 28.4 |
| 8 | 2.5 | 150 | 15 | 25.9 |
| 9 | 2.5 | 150 | 20 | 24.6 |
| 10 | 2.5 | 150 | 20 | 23.8 |
| 11 | 2.5 | 150 | 30 | 27.8 |
| 12 | 2.5 | 150 | 30 | 27.2 |
| 13 | 2.5 | 150 | 45 | 26.9 |
| 14 | 2.5 | 150 | 45 | 29.1 |
| 15 | 2.5 | 150 | 60 | 41.1 |
| 16 | 2.5 | 150 | 60 | 39.6 |
| 17 | 2.5 | 150 | 120 | 109.6 |
| 18 | 2.5 | 150 | 120 | 86.6 |

FIXa aptamer (9.3t) structure

FXa aptamer (11F7T) structure

FIXa aptamer (9D-6) structure

METHOD OF MODULATING THE ACTIVITY OF A NUCLEIC ACID MOLECULE

This application is a continuation-in-part of International Application No. PCT/US2008/004119, filed Mar. 31, 2008, which claims the benefit of U.S. Provisional Application No. 60/920,807, filed Mar. 30, 2007. This application also claims priority from U.S. Provisional Application No. 61/243,078, filed Sep. 16, 2009. The entire contents of International Application No. PCT/US2008/004119, U.S. Provisional Application No. 60/920,807 and U.S. Provisional Application No. 61/243,078 are hereby incorporated by reference.

This invention was made with government support under Grant No. RO1 HL65222 awarded by the National Institutes of Health. The government has certain rights in the invention.

TECHNICAL FIELD

The present invention relates, in general, to agents that modulate the functional activity of nucleic acid molecules and, in particular, to agents that bind therapeutic and/or diagnostic nucleic acid molecules in a sequence independent manner and modulate (e.g., inhibit or reverse) their activity. The invention also relates to compositions comprising such agents and to methods of using same.

BACKGROUND

Aptamers are single-stranded nucleic acid (DNA or RNA) ligands that possess a number of features that render them useful as therapeutic agents. They are relatively small (8 kDa to 15 kDa) synthetic compounds that possess high affinity and specificity for their target molecules (equilibrium dissociation constants ranging from, for example, 0.05-1000 nM). Thus, they embody the affinity properties of monoclonal antibodies and single chain antibodies (scFv's) with the chemical production properties of small peptides. While initial studies demonstrated the in vitro use of aptamers for studying protein function, more recent studies have demonstrated the utility of these compounds for studying in vivo protein function (Floege et al, Am J Pathol 154:169-179 (1999), Ostendorf et al, J Clin Invest 104:913-923 (1999), Dyke, Circulation 114(23):2490-7 (2006), Group, Retina 22(2):143-52 (2002), Group, Opthalmology 110(5):979-86 (2003), Nimjee et al, Mol. Ther. 14(3):408-15 (2006), Nimjee et al, Trends Cardiovasc Med. 15(1):41-5 (2005), Nimjee et al, Annu. Rev. Med. 56:555-83 (2005), Rusconi et al, Nat. Biotechnol. 22(11): 1423-8 (2004)). In addition, animal studies to date have shown that aptamers and compounds of similar composition are well tolerated, exhibit low or no immunogenicity, and are thus suitable for repeated administration as therapeutic compounds (Floege et al, Am J Pathol 154:169-179 (1999), Ostendorf et al, J Clin Invest 104:913-923 (1999), Griffin et al, Blood 81:3271-3276 (1993), Hicke et al, J Clin Invest 106:923-928 (2000), Dyke, Circulation 114(23):2490-7 (2006), Group, Retina 22(2):143-52 (2002), Group, Opthalmology 110(5):979-86 (2003), Nimjee et al, Mol. Ther. 14(3):408-15 (2006), Nimjee et al, Trends Cardiovasc Med. 15(1):41-5 (2005), Nimjee et al, Annu. Rev. Med. 56:555-83 (2005), Rusconi et al, Nat. Biotechnol. 22(11):1423-8 (2004)).

As synthetic compounds, site specific modifications can be made to aptamers to rationally alter their bioavailability and mode of clearance. For example, it has been found that 2'fluoro pyrimidine-modified aptamers in the 10 kDa to 12 kDa size range have a short circulating half-life (~10 minutes) following bolus intravenous administration but that simple chemical modification of the aptamer or conjugation of the aptamer to a high molecular weight inert carrier molecule (e.g., PEG) increases circulating half-life substantially (6-12 hours) (Willis et al, Bioconjug Chem 9:573-582 (1998), Tucker et al, J Chromatogr Biomed Sci Appl 732:203-212 (1999), Watson et al, Antisense Nucleic Acid Drug Dev 10:63-75 (2000)). Bioactive and nuclease resistant single-stranded nucleic acid ligands comprising L-nucleotides have been described (Williams et al, Proc. Natl. Acad. Sci. 94:11285 (1997); U.S. Pat. No. 5,780,221; Leva et al, Chem. Biol. 9:351 (2002)). These "L-aptamers" are reportedly stable under conditions in which aptamers comprising nucleotides of natural strandedness (D-nucleotides) (that is, "D-aptamers") are subject to degradation.

Aptamers can be generated by in vitro screening of complex nucleic-acid based combinatorial shape libraries ($>10^{14}$ shapes per library) employing a process termed SELEX (for Systematic Evolution of Ligands by EXponential Enrichment) (Tuerk et al, Science 249:505-10 (1990)). The SELEX process consists of iterative rounds of affinity purification and amplification of oligonucleotides from combinatorial libraries to yield high affinity and high specificity ligands. Combinatorial libraries employed in SELEX can be front-loaded with 2'modified RNA nucleotides (e.g., 2'fluoro-pyrimidines) such that the aptamers generated are highly resistant to nuclease-mediated degradation and amenable to immediate activity screening in cell culture or bodily fluids. (See also U.S. Pat. No. 5,670,637, U.S. Pat. No. 5,696,249, U.S. Pat. No. 5,843,653, U.S. Pat. No. 6,110,900, U.S. Pat. No. 5,686,242, U.S. Pat. No. 5,475,096, U.S. Pat. No. 5,270,163 and WO 91/19813.)

Over the past decade, the SELEX technology has enabled the generation of high affinity and high specificity antagonists to a myriad of proteins including reverse transcriptases, proteases, cell adhesion molecules, infectious viral particles and growth factors (see Gold et al, Annu Rev Biochem 64:763-97 (1995)). In particular, this technology has been employed to generate potent antagonists of coagulation factors, including factors VIIa, IXa, Xa and thrombin, transcription factors, autoimmune antibodies, cell surface receptors, as well as Von Willebrand factor and GPIIb-IIIa (see, for example, Rusconi et al, Thrombosis and Haemostasis 83:841-848 (2000), White et al, J. Clin Invest 106:929-34 (2000), Ishizaki et al, Nat Med 2:1386-1389 (1996), Lee et al, Nat Biotechnol 15:41-45 (1997), Nimjee et al, Annu. Rev. Med. 56:555-83 (2005)). (See also Published U.S. Application No. 20030083294 and documents cited therein, which documents are incorporated herein by reference as is Published U.S. Application No. 20030083294.)

It has been shown previously that the activity of aptamers can be reversed by using matched antidote oligonucleotides (Dyke, Circulation 114(23):2490-7 (2006), Rusconi et al, Nat Biotechnol. 22(11):1423-8 (2004), Rusconi et al, Nature 419 (6902):90-4 (2002)); Published U.S. Application No. 20030083294). Joachimi et al (J. Am. Chem. Soc. 129:3036-3037 (2007)) have reported that a G-quadruplex-binding porphyrin can be used to control the anticoagulant activity of a G-quadruplex-containing aptamer (the porphyrin binding to guanine-rich motifs in the quadruplex).

The present invention results from the identification of agents (referred to below as "universal antidotes") that can bind therapeutic or diagnostic nucleic acid molecules, such as aptamers, siRNAs, etc., in a sequence independent manner and modulate (e.g., inhibit or reverse) their activity. The universality of the antidotes disclosed herein translates into significant savings in time and cost from the standpoint of drug development. Further, the nature of these antidotes (detailed below) is such that the formation of double-stranded RNA helices is avoided and, therefore, the potential inflammatory response associated therewith.

SUMMARY OF THE INVENTION

The present invention relates to agents that modulate (e.g., inhibit or reverse) the functional (e.g., pharmacological or diagnostic) activity of nucleic acid molecules (e.g., aptamers (D or L), ribozymes, antisense RNAs, internalizing RNAs and RNAi (e.g., siRNAs, microRNAs, and shRNAs), including modified forms of such molecules (e.g., 2'F, 2'OMe, 2'B, 2'I, 2'NH, etc.)). More specifically, the invention relates to agents that bind therapeutic or diagnostic nucleic acid molecules in a sequence independent manner (that is, in a manner that is independent of the nucleotide sequence of the nucleic acid molecule) and modulate (e.g., inhibit or reverse) their activity. These agents can be used to control and/or optimize use of nucleic acids molecules in disease states and other medical settings. The invention also relates to compositions comprising such agents and to methods of using same.

Objects and advantages of the present invention will be clear from the description that follows.

BRIEF DESCRIPTION OF THE DRAWINGS

(FIG. 5A) Primary sequence and predicted secondary structures of FIXa (9.3t) (SEQ ID NO: 1), FXa (11F7T) (SEQ ID NO: 2), VWF (9.3) (SEQ ID NO: 5), FII (9D-14) (SEQ ID NO: 7), VWF (9.14) (SEQ ID NO: 3), FVII (7S-1) (SEQ ID NO: 4), FX (7K-5) (SEQ ID NO: 61 and FIX (9D-6) (SEQ ID NO: 8) aptamers. (FIGS. 5B and 5D) Ability of protamine (2.5 µg per 160 µl) to reverse aptamer 9.3t (150 nM) function in pooled normal human plasma measured using the APTT assay. (FIG. 5C) Ability of protamine (2.5 µg per 160 µl) to reverse aptamer 11F7T (250 nM) function in pooled normal human plasma measured using the APTT assay. (FIG. 5E) Ability of protamine (2.5 µg per 160 µl) to reverse the function of aptamers 9.3t and 11F7T simultaneously in pooled normal human plasma measured using the APTT assay. Data is plotted as the mean+/−standard error of the mean (SEM) for three independent measurements.

(FIG. 6A) The ability of protamine and 11 different polymers (2.5 µg per 160 µl) to reverse aptamer 9.3t (150 nM) function was measured in pooled normal human plasma using the APTT assay. (FIGS. 6B-6E) The ability of CDP (2.5 µg per 160 µl) to reverse (FIG. 6B) aptamer 9.3t function, (FIG. 6C) aptamer 11F7T function, (FIG. 6D) aptamers 9.3t and 11F7T function simultaneously, (FIG. 6E) aptamers R9D-14, 9D-6 and 7K-5 in normal human plasma was measured using the APTT assay. (FIG. 6F) The ability of CDP (2.5 µg per 160 µl) to reverse aptamer 7S-1 function in pooled normal human plasma was measured using the PT assay. The data is plotted as the mean+/−SEM for three independent measurements.

(FIG. 7A) The ability of CDP to reverse VWF aptamer 9.3 function was measured in normal human whole blood using varying concentrations of the polymer and the PFA-100 assay. The data is plotted as the mean+/−SEM for three independent measurements. (FIG. 7B) The ability of PPA-DPA (30 KDa) to reverse VWF aptamer 9.3 function was measured in normal human whole blood using varying concentrations of the polymer and the PFA-100 assay. (FIG. 7C) The ability of CDP (10 µg) to reverse the activity of the VWF aptamer 9.14 (60 nM) aptamer was measured in the PFA-100 assay. The data is plotted as the mean+/−SEM for three independent measurements.

(FIG. 8A) The anticoagulant activity of the cholesterol modified FIXa aptamer 9.3t (Ch-9.3t) in swine (n=5) was measured using the ACT assay. (FIG. 8B) The ability of protamine to reverse Ch-9.3t function in vivo (n=5) was assessed using ACT assay. (FIG. 8C) The ability of CDP to reverse Ch-9.3t function in vivo (n=5) was assessed using ACT assay. The data shown are plotted as the mean+/−SEM for the duplicate measurements from each animal.

(FIG. 9A) Gel electrophoresis of CDP/9.3t mixtures. The ability of the aptamer 9.3t, when mixed with various amounts of CDP, to migrate through a polyacrylamide gel was examined. While the free aptamer migrates through the gel to give a single band at the expected position (lane 2), all aptamer within the CDP-containing samples [CDP-9.3t ratio 0/1 (lane 2), 2/1 (lane 3), 4/1 (lane 4), 6/1 (lane 5), 8/1 (lane 6), and 10/1 (lane 7)] remains within the well, indicative of an inability to migrate through the gel. (FIG. 9B) Dynamic light scattering (DLS) of a CDP/9.3t mixture. While neither CDP alone nor 9.3t aptamer alone show appreciable scattering (average count rate<2 kcps for both and neither gives an effective diameter within the dynamic range of the instrument (2-5000 nm)), a CDP/9.3t mixture (6.7/1 w/w) shows a strong scattering signal (average count rate 591.7 kcps) and a signal within the dynamic range of the instrument (448.9 nm). The gel electrophoresis and DLS data demonstrate an interaction between CDP and 9.3t at the concentrations and ratio used in the swine anticoagulation experiment (FIG. 8).

(FIG. 10A) Percent change in temperature of the animal during the experiment. (FIG. 10B) Percent change in respiratory rate of the animal during the experiment. (FIG. 10C) Percent change in heart rate of the animal during the experiment. (FIG. 10D) Percent change in systolic pressure of the animal during the experiment. (FIG. 10E) Percent change in diastolic pressure of the animal during the experiment. (FIG. 10F) Percent change in blood oxygen level of the animal during the experiment. The data shown are plotted as the mean+/−SEM for the duplicate measurements from each animal. All data points are done in duplicates for each animal.

DETAILED DESCRIPTION OF THE INVENTION

Figures 1A, 1B:
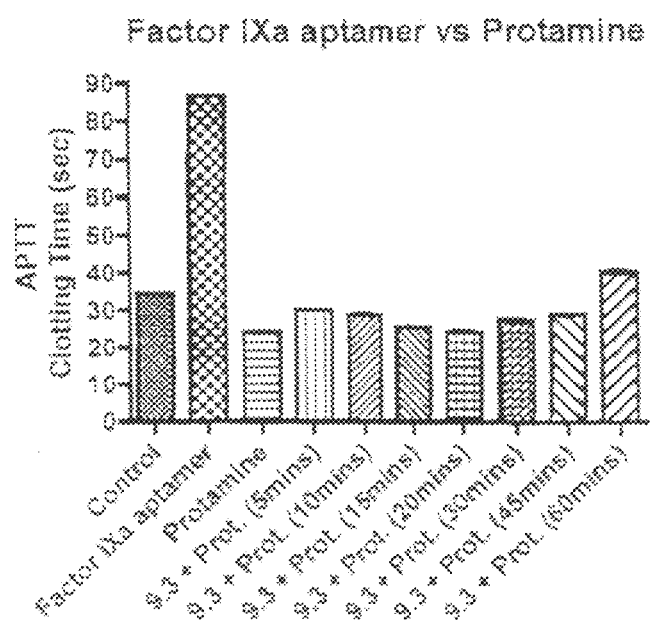
FIGS. 1A and 1B. Protamine reverses Factor IXa aptamer and Factor X aptamer activity in APTT assay. Effect of protamine (2.5 µg) on clotting time of human plasma anti-coagulated with an aptamer ("Ch-9.3t") to human factor IXa (FIG. 1A) or with an aptamer ("11f7t") to human factor Xa (FIG. 1B).

The present invention relates generally to agents ("universal antidotes") (UAs) that can modulate the functional (e.g., pharmacological) activity of nucleic acid molecules (NAMs), including therapeutic and/or diagnostic NAMs, independent of the nucleotide sequence of the NAM. The invention further relates to methods of modulating (e.g., reversing/inhibiting) the effect of pharmacological NAMs by administering such UAs to human or non-human mammals. Additionally, the invention relates to methods of using UAs of the invention to assess the activity of NAMs.

Pharmacological NAMs include, but are not limited to, aptamers, siRNAs, microRNAs, shRNAs, antisense RNAs, aptamer-siRNA chimeras, mRNAs, ribozymes and antago-mirs, that bind a desired target molecule.

Aptamer target molecules include, generally, peptides, proteins, glycoproteins, polysaccharides and nucleic acids, as well as small molecular weight (organic) compounds. More specifically, aptamer target molecules can include enzymes (e.g., proteases, including factors VIIa, IXa, Xa, XIa, thrombin and protein C) as well as zymogens thereof. Aptamer target molecules can also include hormones, receptors (including platelet receptors, e.g., glycoprotein (gp) IIbIIIa, GPIb-IX-V, GPVI, $P2Y_{12}$, and PARs), adhesion molecules (e.g, Von Willebrand factor and collagens) metabolites, cofactors (e.g., Tissue Factor, or coagulation factors Va and VIIIa), transition state analogs, as well as drugs, dyes and toxins. Aptamers can be made using SELEX methodology (see, for example, U.S. Pat. Nos. 5,270,163, 5,817,785, 5,595, 887, 5,496,938, 5,475,096, 5,861,254, 5,958,691, 5,962,219, 6,013,443, 6,030,776, 6,083,696, 6,110,900, 6,127,119, and 6,147,204, see also Published U.S. Application No. 20030083294 and documents cited therein)). Aptamers specific for a wide variety of target molecules are presently available (see, for example, Gold et al, Ann. Rev. Biochem. 64:763 (1995), Nimjee et al, Annu. Rev. Med. 56:555-83 (2005)).

Details of the production of, for example, siRNAs, microRNAs, and antisense RNAs and of methods of using these NAMs in modifying gene expression are described, for example, in Dorsett and Tuschl, Nat Rev Drug Discov. 3(4): 318-29 (2004), Fire et al, Nature 391(6669):806-11 (1998), Grishok et al, Cell 106(1):23-34 (2001), Lagos-Quintana, et al, Rna 9(2):175-9 (2003), Leaman et al, Cell 121(7):1097-108 (2005), Martinez et al, Cell 110(5):563-74 (2002), Meister et al, Rna 10(3):544-50 (2004), Meister and Tuschl, Nature 431 (2006):343-9 (2004), Pfeffer et al, Science 304 (5671):734-6 (2004), Tuschl, Nat Biotechnol. 20(5):446-8 (2002), and Tuschl and Borkhardt, Mol Interv. 2(3):158-67 (2002).

The present invention relates to a method of modulating (e.g., reversing or inhibiting) the activity of a NAM, for example, by altering its conformation and thus its function and/or by sterically blocking binding of the NAM to its target molecule. In accordance with the invention, the UA can be contacted with the targeted NAM, for example, under conditions such that it binds to the NAM and modifies the interaction between the NAM and its target molecule. The UA can also interfere with the binding of the NAM to its target molecule through charge interaction. Modification of the interaction between the NAM and its target molecule can result from, for example, modification of the NAM structure as a result of binding by the UA. The UA can bind the free NAM and/or the NAM bound to its target molecule.

UAs of the invention include pharmaceutically acceptable member(s) of a group of positively charged compounds, including proteins, lipids, and natural and synthetic polymers that can bind NAMs in, for example, biologically fluids.

Proteinaceous UAs of the invention include protamines, a group of proteins that yield basic amino acids on hydrolysis and that occur combined with nucleic acid in the sperm of fish, such as salmon. Protamines are soluble in water, are not coagulated by heat, and comprise arginine, alanine and serine (most also contain proline and valine and many contain glycine and isoleucine). In purified form, protamine has been used for decades to neutralize the anticoagulant effects of heparin. UAs of the invention also include protamine variants (e.g., the +18RGD variant (Wakefield et al, J. Surg. Res. 63:280 (1996)) and modified forms of protamine, including those described in Published U.S. Application No. 20040121443. Other UAs of the invention include protamine fragments, such as those described in U.S. Pat. No. 6,624,141 and U.S. Published Application No. 20050101532. UAs of the invention also include, generally, peptides that modulate the activity of heparin, other glycosaminoglycans or proteoglycans (see, for example, U.S. Pat. No. 5,919,761). The invention further includes pharmaceutically acceptable salts of the above-described UAs, as appropriate, including sulfate salts.

Proteinaceous UAs of the invention also include DNA and/or RNA reactive antibodies. For example, anti-nuclear antibodies, such as those indicative of lupus erythematosis, Sjögren's syndrome, rheumatoid arthritis, autoimmune hepatitis, scleroderma, polymyositis and dermatomyositis, can be used. Specific examples of antibodies that recognize RNA/DNA include those that are described by Kitagawa et al (Mol. Immunol. 19(3):413-20 (1982)), Boguslawski et al (J. Immunol. Methods 89(1):123-30 (1986)), Williamson et al (Proc. Natl. Acad. Sci. 98(4):1793-98 (2001)), and Blanco et al (Clin. Exp. Immunol. 86(1):66-70 (1991)).

In addition, heterogeneous nuclear ribonucleoproteins (HNRPs) can also be used in accordance with the invention. Cationic peptides that bind nucleic acids in a sequence-independent manner are suitable for use. For example, a chimeric peptide synthesized by adding nonamer arginine residues at the carboxy terminus of RVG (to yield RVG-9R) has been described by Kumar et al (Nature 448:39-43 (2007)). Viral proteins that package (e.g., coat) DNA or RNA (e.g., HIV gag protein), and peptides derived therefrom, can also be used in the present methods.

Cationic lipids can also be used as UAs in accordance with the invention. Suitable cationic lipids include those described by Morille et al (Biomaterials 29:3477 (2008)) (e.g., linear poly(ethyleneimine) (PEI), poly(L-lysine) (PLL), poly(amidoamine) (PAMAM) dendrimer generation 4, chitosan, DOTMA, DOTAP, DMRIE, DOTIM, DOGS, DC-Chol, BGTC and DOPE).

UAs of the invention also include intercalating agents. Examples include ethidium bromide, proflavine, daunomycin, doxorubicin and thalidomide. Porphyrins that bind nucleic acids in a sequence independent manner can also be used in accordance with the invention. Porphyrins that bind guanine-rich motifs in G-quadruplexes (as described by, for example, Joachimi et al (J. Am. Chem. Soc. 129:3036 (2007)) do not bind in an independent manner and thus are not within the scope of the invention.

Preferred UAs of the invention include polycationic polymers or peptides. Preferred polycationic polymers include biocompatible polymers (that is, polymers that do not cause significant undesired physiological reactions) that can be either biodegradable or non-biodegradable polymers or blends or copolymers thereof. Examples of such polymers include, but are not limited to, polycationic biodegradable polyphosphoramidates, polyamines having amine groups on either the polymer backbone or the polymer side chains, nonpeptide polyamines such as poly(aminostyrene), poly (aminoacrylate), poly(N-methyl aminoacrylate), poly(N-ethylaminoacrylate), poly(N,N-dimethyl aminoacrylate), poly(N,N-diethylaminoacrylate), poly(aminomethacrylate), poly(N-methyl amino-methacrylate), poly(N-ethyl aminomethacrylate), poly(N,N-dimethyl aminomethacrylate), poly(N,N-diethyl aminomethacrylate), poly(ethyleneimine), polymers of quaternary amines, such as poly(N,N,N-trimethylaminoacrylate chloride), poly(methyacrylamidopropyl-trimethyl ammonium chloride); natural or synthetic polysaccharides such as chitosan, cyclodextrin-containing polymers, degradable polycations such as poly[alpha-(4-aminobutyl)-L-glycolic acid] (PAGA); polycationic polyurethanes, polyethers, polyesters, polyamides, polybrene, etc. Particularly preferred cationic polymers include CDP, CDP-Im, PPA-DPA, PAMAM and HDMBr. (See U.S. Pat. Nos. 7,270,808, 7,166,302, 7,091,192, 7,018,609, 6,884,789, 6,509,323, 5,608,015, 5,276,088, 5,855,900, U.S. Published Appln. Nos. 20060263435, 20050256071, 200550136430, 20040109888, 20040063654, 20030157030, Davis et al, Current Med. Chem. 11(2) 179-197 (2004), and Comprehensive Supramolecular Chemistry vol. 3, J. L. Atwood et al, eds, Pergamon Press (1996).)

UAs of the invention can include compounds of types described in Table 1, or derivatives thereof. Several of the compounds described in Table 1 contain cationic-NH groups permitting stabilizing charge-charge interactions with a phosphodiester backbone. Nucleic acid binding agents of the invention containing secondary amines can include, for example, 5-350 such groups (e.g., 5-300, 5-250, 5-200, 5-100, 5-50, 50-100, 50-200, 50-300, 50-350, 100-200, 100-300, 100-350, 200-350, 200-300, or 250-350), and can have a molecular weight in the range of, for example, 2,000 to 50,000 (e.g., 10,000 to 50,000 or 20,000 to 40,000).

TABLE 1

| Compound | Abbreviation | Molecular structure | | Remark |
|---|---|---|---|---|
| Poly-L-lysine | PLL | 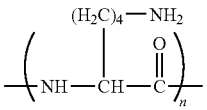 | | 1. Commercially available. 2. Carbonyl moiety (—C=O) which could permit additional stabilization to the complex through hydrogen bonds with DNA. |
| Poly-L-ornithine | PLO | 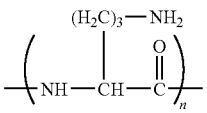 | | 1. Commercially available. 2. Carbonyl moiety (—C=O) which could permit additional stabilization to the complex through hydrogen bonds with DNA. |
| Polyphosphoramidate polymer series | PPA-SP PPA-BA PPA-EA PPA-MEA PPA-DMA PPA-DEA PPA-TMA PPA-DPA | 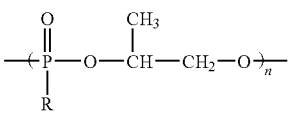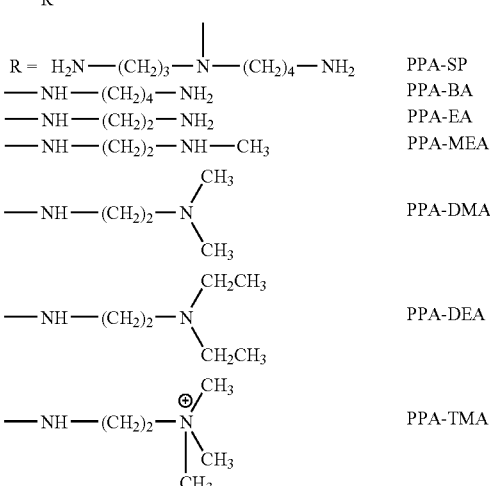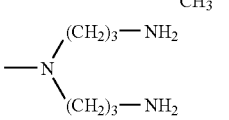 | PPA PPA-SP PPA-BA PPA-EA PPA-MEA PPA-DMA PPA-DEA PPA-TMA PPA-DPA | 1. Polymers with an identical backbone but different side chains ranging from primary to quaternary amines. Provide a platform for a systematic study. 2. Lower cytotoxicity compared with polyethylenimine (PEI) and poly-L-lysine (PLL). |

TABLE 1-continued

| Compound | Abbreviation | Molecular structure | Remark |
| --- | --- | --- | --- |
| Polyphosphoramidate diprophylamine-poly ethylene glycol copolymer | PPA-DPA-b-PEG$_{2000}$ | PEG—O—(P(=O)(N((CH$_2$)$_3$—NH$_2$)((CH$_2$)$_3$—NH$_2$))—O—CH(CH$_3$)—CH$_2$—O)$_n$ | 1. a copolymer of PPA-DPA and PEG. |
| Polyethyleneimine | PEI | —(CH$_2$—CH$_2$—NH)$_n$— | 1. Commercially available. 2. PEI with branched structure condenses DNA to a greater extent than linear ones. 3. high cytotoxicity. |
| Ionene e.g. polybrene | | —(N$^+$(CH$_3$)$_2$—(CH$_2$)$_3$—N$^+$(CH$_3$)$_2$—(CH$_2$)$_6$)$_n$— 2 Br$^-$ | 1. Commercially available. 2. Have high charge density. |
| Natural polyamine e.g. Putrescine Spermine Spermidine | | H$_2$N—(CH$_2$)$_4$—NH$_2$<br>H$_2$N—(CH$_2$)$_3$—NH—(CH$_2$)$_4$—NH—(CH$_2$)$_3$—NH$_2$<br>H$_2$N—(CH$_2$)$_4$—NH—(CH$_2$)$_3$—NH$_2$ | 1. Commercially available. 2. The most extensive work on their binding with DNA has been carried out and have remarkable effects on the DNA condensation. |
| Poly(allylamine) | PAL | —(CH$_2$—CH(CH$_2$—NH$_2$))$_n$— | 1. Commercially available. 2. Highly positive charged 3. Low toxicity. |
| Peptide nucleic acid | PNA | (—CH$_2$—N(CH$_2$—C(=O)—Base)—CH$_2$—C(=O)—NH—CH$_2$—)$_n$ | 1. Commercially available. 2. Binding through Watson-crick base pairing, thus binding is typically stronger and more rapid. |

TABLE 1-continued

| Compound | Abbreviation | Molecular structure | Remark |
|---|---|---|---|
| Poly (porphyrin) or Porphyrin ladder | e.g. poly (H₂(p-TAPP poly (por) A-AN)) | (structure of porphyrin polymer with trimethylammonium phenyl substituents and phenyl-ethynyl linkages); (-CH₂-CH(COO-POR)-)ₙ | |
| Poly (2-Methacryloyloxyethyl phosphorylcholine) Dendrimers | PMPC | (-CH₂-C(CH₃)(C(=O)-O-CH₂-CH₂-O-P(O)(O⁻)-O-CH₂-CH₂-N⁺(CH₃)₃)-)ₙ | |
| e.g. poly-amidoamine dendrimer | PAMAM Dendrimer G2 | (branched PAMAM G2 dendrimer structure) | 1. Commercially available. 2. Branched spherical shape and a high density surface charge. 3. Low cytotoxicity. |

TABLE 1-continued

| Compound | Abbreviation | Molecular structure | Remark |
|---|---|---|---|
| e.g. poly-propyleneimine dendrimer | PPI dendrimer | 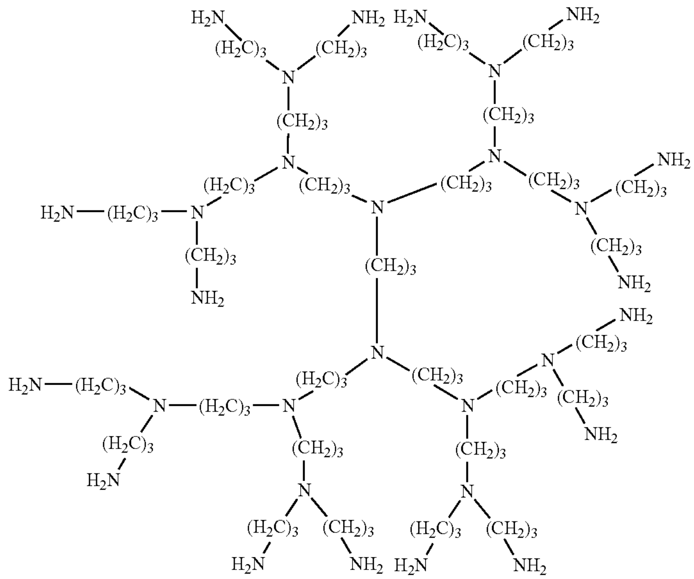 | 1. A class of amine-terminated polymers, demonstrated to be efficient gene delivery vectors. 2. Low cytotoxicity in a wide range of mammalian cell lines. 3. Unique molecular structures, with defined molecular weight, surface charge and surface functionality. These properties of dendrimers provide a platform for a systematic study. |
| Partially deacetylated Chitin | | 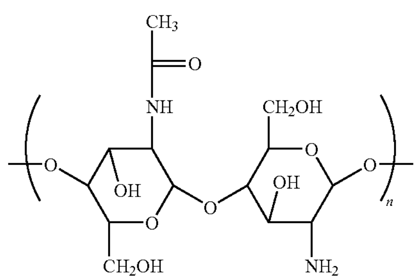 | 1. Commercially available. |
| Cyclodextrin grafted branched PEI or linear PEI (α-CD: six sugar ring β-CD: seven sugar ring γ-CD: eight sugar ring) | CD-bPEI CD-lPEI | 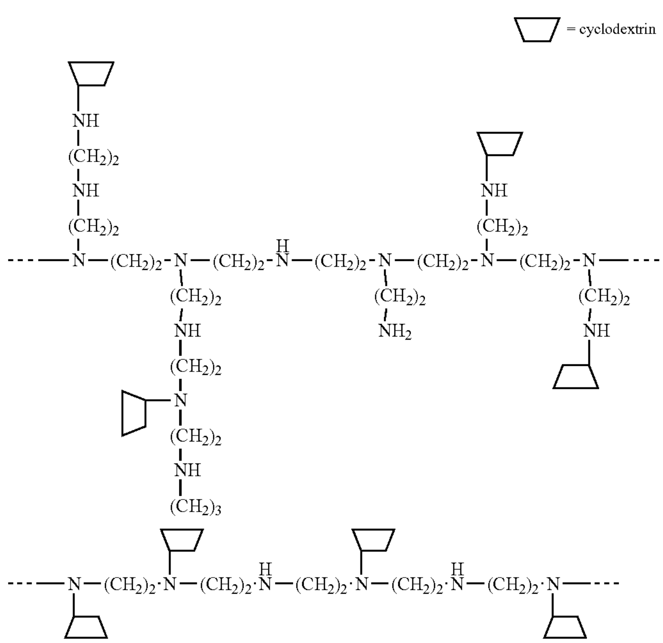 | 1. Their IC50's are 2-3 orders of magnitude higher than the corresponding non-cyclodextrin-based polymer. |

TABLE 1-continued

| Compound | Abbreviation | Molecular structure | Remark |
|---|---|---|---|
| Cyclodextrin Containing Polymers | CDP | 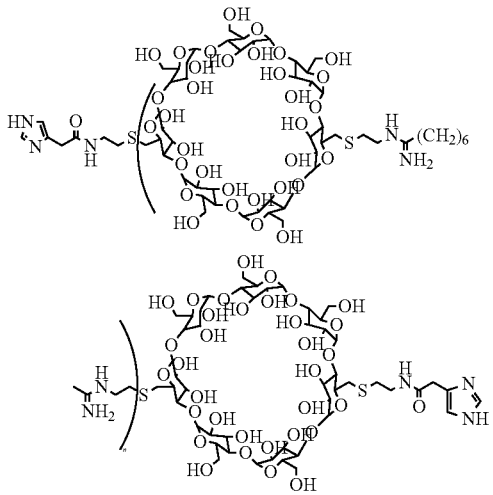 | |
| | CDP-Im | 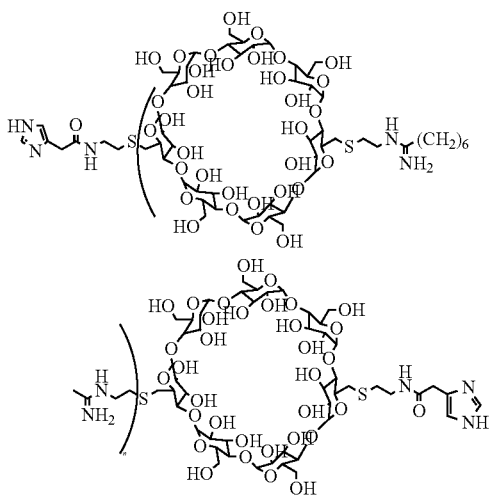 | |

Advantageously, the binding affinity of a UA of the invention for a NAM, expressed in terms of Kd, is in the pM to $\mu$M range, preferably, less than or equal to 50 nM; expressed in terms of binding constant (K), the binding affinity is advantageously equal to or greater than $10^5 M^{-1}$, preferably, $10^5 M^{-1}$ to $10^8 M^{-1}$, more preferably, equal to or greater than $10^6 M^{-1}$. Thus, the binding affinity of the UA can be, for example, about $1 \times 10^5 M^{-1}$, $5 \times 10^5 M^{-1}$, $1 \times 10^6 M^{-1}$, $5 \times 10^6 M^{-1}$, $1 \times 10^7 M^{-1}$, $5 \times 10^7 M^{-1}$; or about 10 pM, 100 pM, 1 nM, 10 nM, 100 nM, 1 $\mu$M, 10 $\mu$M, 100 $\mu$M. "K" and "Kd" can be determined by methods known in the art, including surface plasmon resonance or a real time binding assay such as Biacore.

Certain UAs of the invention, for example, protamine, can be isolated from natural sources (Kossel, The Protamines and Histones (Longmans, NY (1928); Felix et al, Z. Physiol. Chem. 330:205 (1963); Ando et al, Int. J. Prot. Res. 1:221 (1969); Felix, Adv. Prot. Chem. 15:1 (1960). Alternatively, proteinaceous UAs can be produced recombinantly, chemically, or synthetically. UAs described in Table 1 are available commercially and/or can be produced using art-recognized techniques.

Standard binding assays, for example, can be used to screen for preferred UAs of the invention (e.g., using BIA-CORE and isothermal microcalorimetric assays). That is, test compounds (e.g., protamine fragments or variants or modified forms of protamine) can be contacted with the NAM (e.g., aptamer, etc.) to be targeted under conditions favoring binding and a determination made as to whether the test compound in fact binds the NAM. Test compounds that are found to bind the NAM can then be analyzed in an appropriate bioassay (which will vary depending on the NAM and its target molecule) to determine if the test compound can affect the binding of the NAM to its target molecule and/or modulate (e.g., reverse) the activity of the NAM or modify the NAM and its activity in a functional assay. Test compounds that bind a NAM of one nucleotide sequence can be screened against a NAM having a different nucleotide sequence to thereby identify compounds that bind in a sequence independent manner.

The UAs of the invention can be used, for example, to reverse the anticoagulant and antithrombotic effects of NAMs (e.g, aptamers, etc.) that target components of the coagulation pathway, particularly antagonists of the tissue factor (TF)/factor VIIa (FVIIa), factor VIIIa (FVIIIa)/factor IXa (FIXa), factor Va (FVa)/factor Xa (Fxa) enzyme complexes and platelet receptors such as GPIIb-IIIa and GPVI, factors involved in promoting platelet activation such as Gas6, Von Willebrand factor, collagen, factors involved in promoting or maintaining fibrin clot formation such as PAI-1 (plasminogen activator inhibitor 1) or coagulation factor XIIIa (FXIIIa), and additional factors involved in promoting or preventing fibrin clot formation such as ATIII (anti-thrombin III), thrombin or coagulation factor XIa (FXIa).

UAs of the invention are administered in an amount sufficient to modulate (e.g., reverse) the NAM activity. Several clinical scenarios exist in which the ability to rapidly reverse the activity of an antithrombotic or anticoagulant NAM is desirable. A first case is when anticoagulant or antithrombotic treatment leads to hemorrhage, including intracranial or gastrointestinal hemorrhage. A second case is when emergency surgery is required for patients who have received antithrombotic treatment. This clinical situation arises in a low percentage of patients who require emergency coronary artery bypass grafts while undergoing percutaneous coronary intervention under the coverage of GPIIb/IIIa inhibitors. Current practice in this situation is to allow for clearance of the compound (for small molecule antagonists such as eptifibatide), which may take 2-4 hours, or platelet infusion (for Abciximab treatment). A third case is when an anticoagulant NAM is used during a cardiopulmonary bypass procedure. Bypass patients are predisposed to post operative bleeding. In each case, acute reversal of the anticoagulant effects of a compound via an antidote (e.g., a proteinaceous modulator of the invention) allows for improved, and likely safer, medical control of the anticoagulant or antithrombotic compound. Similarly, the UAs of the invention can be used when a patient on an anthrombotic is involved in an accident or suffers intracranial hemorrhage and blood loss cannot otherwise be stopped.

UAs of the invention can be used in any of a variety of situations where control of NAM activity is desired. The targeting of antithrombotic and anticoagulant NAMs is only one example. UAs of the invention can also be used, for example, to modulate (e.g., reverse) the immunosuppressive effect of NAMs that target interleukin, for example, in patients subject to infection. The present UAs can be used, for example, to reverse the immunostimulatory effects of NAMs that target CTLA4 in patients at risk of developing autoimmunity.

The UAs of the invention can also be used to inhibit NAMs that activate the immune system. If, for example, a patient goes into systemic shock because of over activated immune response due to NAMs binding to immune activating cells, UAs of the invention can be used to reverse the effect.

UAs of the invention can be used to modulate (e.g. reverse) the effects of NAMs that target receptors involved in the transmission of the nerve impulse at the neuromuscular junction of skeletal muscle and/or autonomic ganglia (e.g., nicotinic acetylcholine or nicotinic cholinergic receptors). Such NAMs can be made to produce muscular relaxation or paralysis during anesthesia. Agents that block the activity of acetylcholine receptors (agents that engender neuromuscular blockade) are commonly used during surgical procedures, and it is preferred that the patients regain muscular function as soon as possible after the surgical procedure is complete to reduce complications and improve patient turnover in the operating arenas. Therefore, much effort has been made to generate agents with predictable pharmacokinetics to match the duration of the drug activity to the anticipated duration of the surgical procedure. Alternatively, UAs of the invention can be used to provide the desired control of the activity of the neuromuscular blocker, and thus reduce the dependence on the patient's physiology to provide reversal of the neuromuscular blocking agent.

UAs of the invention can be used to modulate (e.g. reverse) the effects of NAMs that target growth factors (e.g., PDGF or VEGF). Such NAMs can be used in the treatment of tumors and in the treatment of inflammatory proliferative diseases. Since growth factors play systemic roles in normal cell survival and proliferation, NAM treatment can result in a breakdown of healthy tissue if not tightly regulated (e.g., patients receiving NAM that target angiopoietin I can be subject to hemorrhaging). UAs of the invention can be used to provide the necessary regulation.

UAs of the invention can be used to modulate (e.g. reverse) the effect of NAMs that target small molecules, such as glucose. Hypoglycemia can be avoided in patients receiving glucose-targeted NAMs to regulate glucose uptake using the modulators of the invention. The present UAs can also be used to regulate the activity of NAMs directed against members of the E2F family, certain of which are pro-proliferative, certain of which are repressive. The UAs of the invention can be used to "turn off" such NAMs at desired points in the cell cycle.

UAs of the invention can also be used to reverse the binding of NAMs bearing radioactive, cytotoxic or other therapeutic moieties to target tissue (e.g., neoplastic tissue) and thereby, for example, facilitate clearance of such a moiety from a patient's system and thereby control or limit patient exposure.

The UAs of the invention can also be used to reverse the binding of NAMs labeled with detectable moieties (used, for example, in imaging (e.g., PET or CT) or cell isolation or sorting) to target cells or tissues (see, generally, Hicke et al, J. Clin. Invest. 106:923 (2000); Ringquist et al, Cytometry 33:394 (1998)). This reversal can be used, for example, to expedite differential imaging of the detectable moiety. For example, an aptamer that bears a detectable label and that recognizes, for instance, cells of a tumor or a thrombosis, can be administered to a patient under conditions such that the labeled aptamer binds to the tumor or clot. Administration of a UA of the invention can rapidly reverse the binding of the labeled aptamer to its target. The ability to effect this rapid reversal makes possible differential real time imaging of the tumor or clot.

The UAs of the invention can also be used in in vitro settings to modulate (e.g., inhibit) the effect of a NAM (e.g., aptamer, etc.) on a target molecule. For example, a UA of the invention can be used to modulate (e.g., reverse) the effect of a NAM on a particular target molecule, present in a mixture of target molecules.

The UAs of the invention (including nucleic acid binding polymers incorporated into microparticles or nanoparticles or beads), or pharmaceutically acceptable salts thereof, can be formulated into pharmaceutical compositions that can include, in addition to the UA, a pharmaceutically acceptable carrier, diluent or excipient. "Pharmaceutically acceptable" with respect to a component, such as a salt, carrier, excipient or diluent of a composition according to the present invention is a component that is compatible with the other ingredients of the composition, in that it can be combined with the UA of the present invention without eliminating the biological activity of the UA, and is suitable for use with subjects as provided herein without undue adverse side effects (such as toxicity, irritation, and allergic response). Side effects are "undue" when their risk outweighs the benefit provided by the composition comprising the UA. Examples of such carriers include, but are not limited to, aqueous solutions, aqueous or non-aqueous solvents, suspensions, emulsions, gels, pastes, and the like. As known to those skilled in the art, a suitable pharmaceutically acceptable carrier can comprise one or more substances, including but not limited to, water, buffered water, medical parenteral vehicles, saline, 0.3% glycine, aqueous alcohols, isotonic aqueous buffer; and can further include one or more substances such as water-soluble polymer, glycerol, polyethylene glycol, glycerin, oils, salts such as sodium, potassium, magnesium and ammonium, phosphonates, carbonate esters, fatty acids, saccharides, polysaccharides, glycoproteins (for enhanced stability), excipients, and preservatives and/or stabilizers (to increase shelf-life or as necessary and suitable for manufacture and distribution of the composition).

The precise nature of the compositions of the invention will depend, at least in part, on the nature of the UA and the route of administration. Optimum dosing regimens can be readily established by one skilled in the art and can vary with the UA, the NAM, the patient and the effect sought. Generally, the NAM and UA can be administered orally, transdermally, IV, IM, IP, SC, or topically, as appropriate.

The amount of UA administered is sufficient to inhibit or reverse binding of a NAM to its target. Preferably, at least 50% of the NAMs are inhibited from binding target molecules or, for those NAMs bound to target molecules, are interrupted and freed from binding ("reversal") their target molecules, as compared to binding in the absence of the UA.

Furthermore, because the antidote activity is durable, once the desired level of modulation of the NAM by the antidote is achieved, infusion of the antidote can be terminated, allowing residual antidote to clear the human or animal. This allows for subsequent re-treatment of the human or non-human animal (e.g., farm animal such as a cow, pig, horse, goat or sheep, or companion animal such as a dog or cat) with the NAM as needed.

Proteinaceous UAs of the invention can also be produced in vivo following administration of a construct comprising a sequence encoding the proteinaceous UA (Harrison, Blood Rev. 19(2):111-23 (2005)).

Certain aspects of the invention are described in greater detail in the non-limiting Examples that follows. Incorporated by reference is the following citation that describes APTT and other clotting assays: Quinn et al, J. Clin. Lab. Sci. 13(4):229-238 (2000). This review describes the properties and biochemistry of various clotting assays including APTT, PT and thrombin time assays, and their use in diagnosing coagulopathies.

EXAMPLE I

Millions of individuals have received protamine, a group of positively charged proteins, to reverse the blood thinning effects of heparin, particularly following cardiopulmonary bypass surgery. A crystal structure study on an RNA aptamer that binds human thrombin showed that the aptamer bound to thrombin in a similar location as heparin. To test the hypothesis that aptamers may have other properties similar to heparin, studies were undertaken to determine if aptamer activity could be neutralized with protamine, since heparin activity can be reversed using protamine.

To test this possibility, human plasma was anticoagulated with two different aptamers, one to human factor IXa (termed CH-9.3t (37 nt, 2'fluoropyrimidine modified ssRNA molecule with a cholesterol moiety on the 5' end, 3'idt) 9.3t (same as CH-9.3t except no carrier)) and a second one to human factor Xa (termed 11f7t (37 nt long, 2'fluoropyrimidine modified RNA molecule)).

Figure 2:
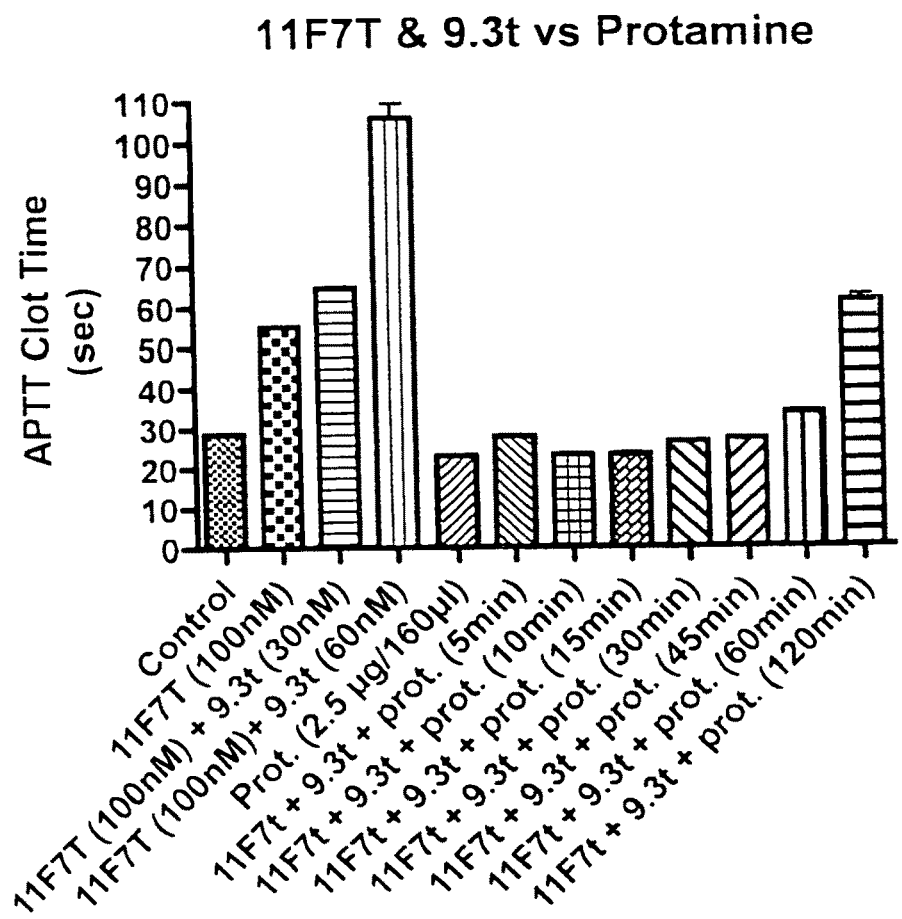
FIG. 2. Protamine reverses both aptamers' activity.

As shown in FIG. 1, addition of the aptamers to human plasma (150 nM for Ch9.3t and 250 nM 11f7t) significantly increased the clotting time as measured in an aPTT assay. In the case of the factor IXa aptamer, clotting time increased from a baseline of approximately 34 seconds to approximately 87 seconds (FIG. 1A). Addition of protamine (2.5 μg) to the plasma after it had been anticoagulated with the factor IXa aptamer returned the clotting time to normal within 5 minutes following addition. This reversal was maintained for at least an hour. Similarly, the factor Xa aptamer (250 nM) increased the clotting time of normal human plasma in the aPPT assay from approximately 28 seconds to approximately 97 seconds. As shown in FIG. 1B, administration of protamine (2.5 μg) totally reversed the activity of the factor Xa aptamer within 5 minutes. (See also FIG. 2.)

EXAMPLE II

Table 2 includes a summary of data resulting from UA vs aptamer experiments (see Example I above (Bi-9.3t (37 nt, 2'fluoropyrimidine modified ssRNA with biotin on the 5' end)).

TABLE 2

Universal Antidote vs Aptamer Experiments

| Aptamer (150 nM) | Antidote | APTT clotting time (sec) | Reversal | Comments |
|---|---|---|---|---|
| 0 | 0 | 34.5 | | These are abbreviated results. |
| 9.3t-Bi | 0 | 86.6 | | All the concentrations are optimized. |
| 0 | Protamine (2.5 ug/well) | 24 | | |
| 9.3t-Bi | Protamine (2.5 ug/well) | 30.3 | Yes | |
| 0 | 0 | 30.5 | | |
| 9.3t-Bi | 0 | 85.2 | | |
| 0 | Poly-L Lysine (5 KDa)(1.3 ug/well) | 30.7 | | |
| 9.3t-Bi | Poly-L Lysine (5 KDa) (1.3 ug/well) | 81 | No | |
| 0 | 0 | 33.5 | | |
| 9.3t-Bi | 0 | 83.1 | | |
| 0 | Poly-L Lysine (300 KDa)(1.3 ug/well) | 30.7 | | |
| 9.3t-Bi | Poly-L Lysine (300 KDa) (1.3 ug/well) | 39.4 | Yes | |
| 0 | 0 | 31.3 | | |
| 9.3t-Bi | 0 | 76.1 | | |
| 0 | Poly-L Lysine (360 KDa)(1.3 ug/well) | 37.9 | | |
| 9.3t-Bi | Poly-L Lysine (360 KDa) (1.3 ug/well) | 43.9 | Yes | |
| 0 | 0 | 36.2 | | |
| 9.3t-Bi | 0 | 91.1 | | |
| 0 | Spermine (1.3 ug/well) | 63.8 | | |

TABLE 2-continued

Universal Antidote vs Aptamer Experiments

| Aptamer (150 nM) | Antidote | APTT clotting time (sec) | Reversal | Comments |
|---|---|---|---|---|
| 9.3t-Bi | Spermine (1.3 ug/well) | 72.7 | NO | Did not work b/w 1.3 ug/well-10 ug/well |
| 0 | 0 | 28.8 | | |
| 9.3t-Bi | 0 | 78.7 | | |
| 0 | PPA-DPA 8 KDa (65 ug/well) | 58.2 | | |
| 9.3t-Bi | PPA-DPA 8 KDa (1.3 ug/well) | 63.9 | NO | Did not work b/w 1.3 ug/well-65 ug/well |
| 0 | 0 | 27.9 | | |
| 9.3t-Bi | 0 | 69.9 | | |
| 0 | PPA-DPA 30 KDa (1.3 ug/well) | 28.3 | | |
| 9.3t-Bi | PPA-DPA 30 KDa (1.3 ug/well) | 36.2 | Yes | |
| 0 | 0 | 27.5 | | |
| 9.3t-Bi | 0 | 75.9 | | |
| 0 | Peg-b-PPA (1.3 ug/well) | 24.8 | | |
| 9.3t-Bi | Peg-b-PPA (1.3 ug/well) | 58.8 | No | Did not work b/w 1.3 ug/well-65 ug/well |

EXAMPLE III

The Platelet Function Analyzer (PFA-100). The PFA-100 is a bench top instrument that uses whole blood and simulates platelet function under high shear stress conditions. In this experiment, disposable cartridges coated with Collagen/ADP were filled with 840 microliters of whole human blood (collected in 10 ml sodium heparin tubes) and placed into the PFA-100. The standard test protocol is followed and each dilution point is done in duplicates. For antidote experiments, 50 nM of vWF aptamer R9.3 was incubated with the whole blood for 5 minutes followed by the addition of antidote. The blood was than placed in PFA-100 and the test was run.

Figure 3:
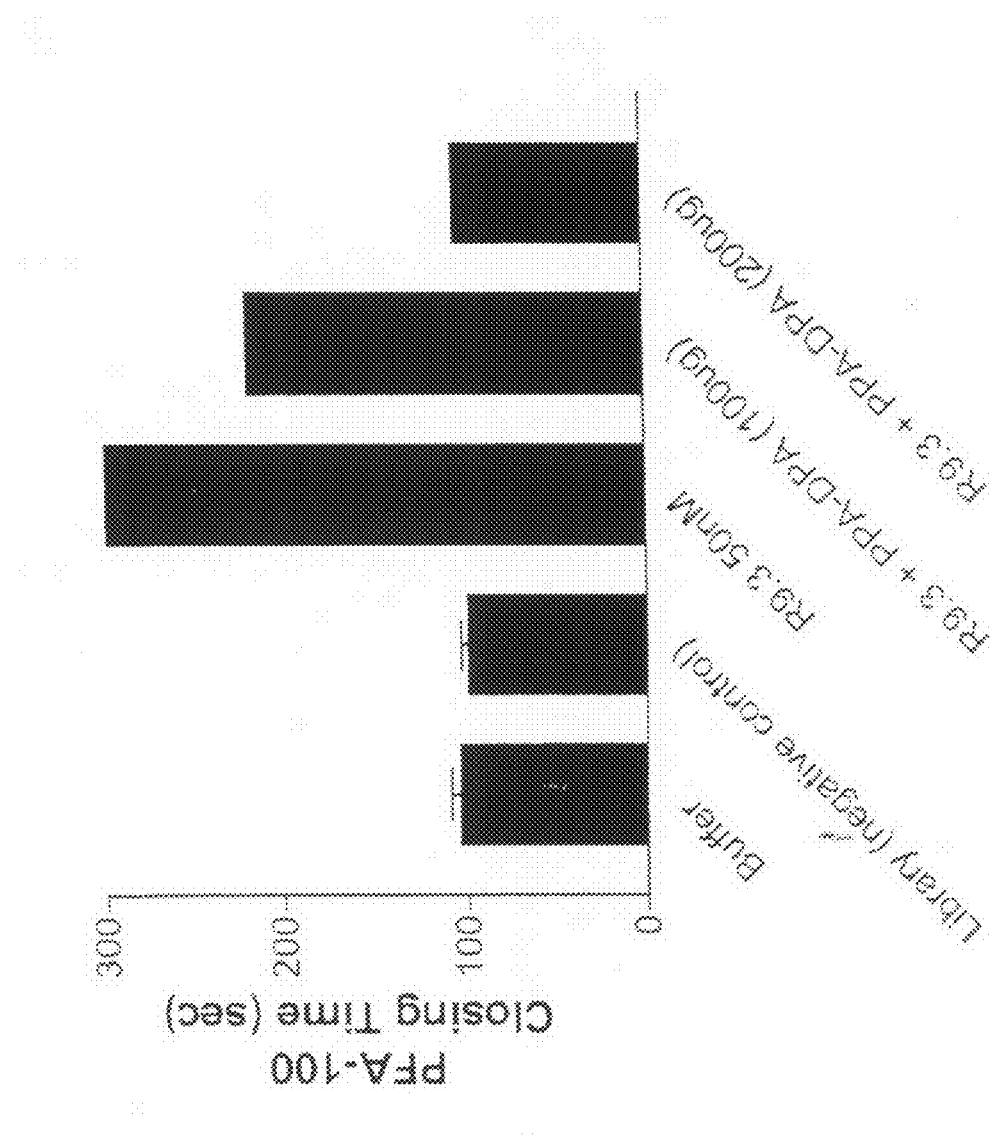
FIG. 3. PPA-DPA reverses Von Willebrand R9.3 aptamer activity.

During the test, blood in the cartridge is aspirated under constant negative pressure from the reservoir, through a capillary, passing a microscopic aperture cut into the membrane. The shear stress rate during this process reaches 5000-6000 $s^{-1}$ and along with the platelet activators (i.e. Collagen/ADP) present on the membrane, initiates platelet activation, adhesion and aggregation. These processes cause the formation of a platelet plug on the microscopic aperture and blood flow through the capillary ceases. The platelet function is measured as the time it takes to form the aperture occlusion. Although the PFA-100 is sensitive to many variables that affect platelet function, a number of studies revealed that it is most sensitive to certain platelet receptor defects (mainly GPIb-IX-V and GP IIbIIIa) and VWF defects. (See FIG. 3.)

EXAMPLE IV

Experimental Details

Swine (2.5-3.5 kg) were randomly assigned to treatment groups. For all groups, anesthesia was induced by intramuscular injection of ketamine (22 mg/kg) and acepromazine (1.1 mg/kg). A catheter was then placed in the ear vein, through which anesthesia was maintained with fentanyl, first with a 100 μg/kg bolus, and then with a continuous infusion of 60 $\mu g \cdot kg^{-1} \cdot h^{-1}$. The swine were then intubated and mechanically ventilated. Following placement of the esophageal or rectal temperature probe and $SPO_2$ monitor, the femoral artery and vein were cannulated. The arterial line was used as a means to continuously monitor mean arterial blood pressure and heart rate, as well as removal of blood samples for evaluation of ACT. After determining baseline ACT values, the venous line was used to administer the Factor IXa aptamer (0.5 mg/kg). Blood samples were then drawn from the arterial line at 5, 15, and 30 minutes post aptamer administration. The ACT values were measured by using Hemochron Jr. Signature Microcoagulation System (ITC, Edison N.J.). For experiments involving antidote administration, 40 mg protamine (10 mg/mL) was given over five minutes via the femoral vein catheter at 30 minutes post aptamer injection. For all animals, subsequent blood samples were at taken at 35, 40, 55, 60, 75, and 90 minutes post aptamer administration. All data points are done in duplicate per animal. At the closure of the experiment, swine were euthanized with Euthasol (175 mg/kg) via femoral vein.

All animals received humane treatment in accordance with the *Guide for the Care and Use of Laboratory Animals* published by the National is Institutes of Health, as approved by the Duke University Animal Care and Use Committee.

Results

Figure 4A:
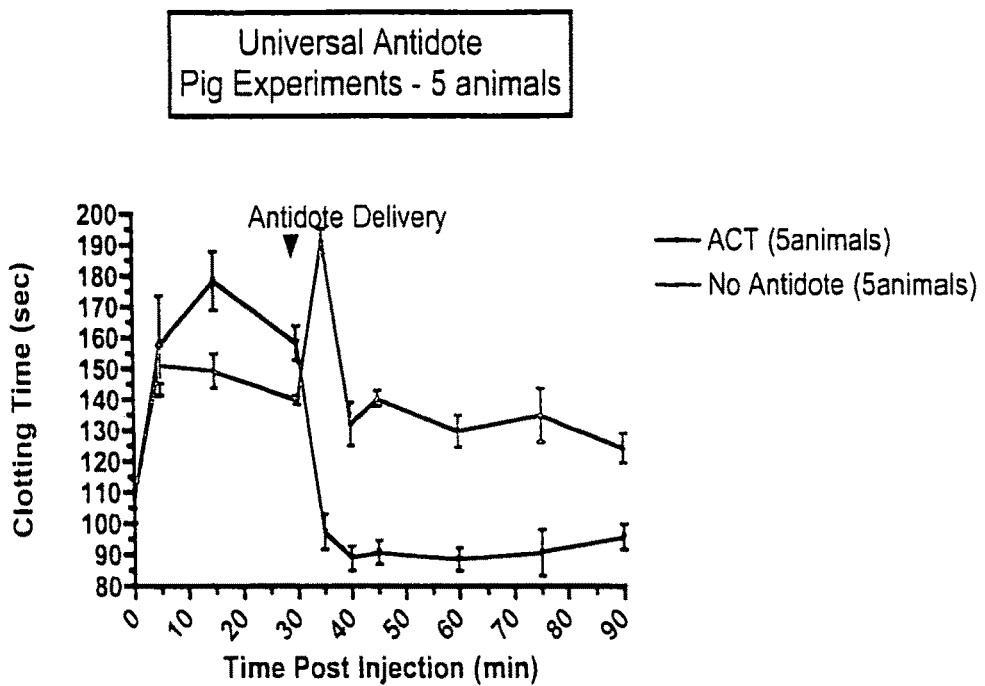
FIGS. 4A-4C. Protamine reverses Factor IXa aptamer in pig anticoagulation model.
Figure 4B:
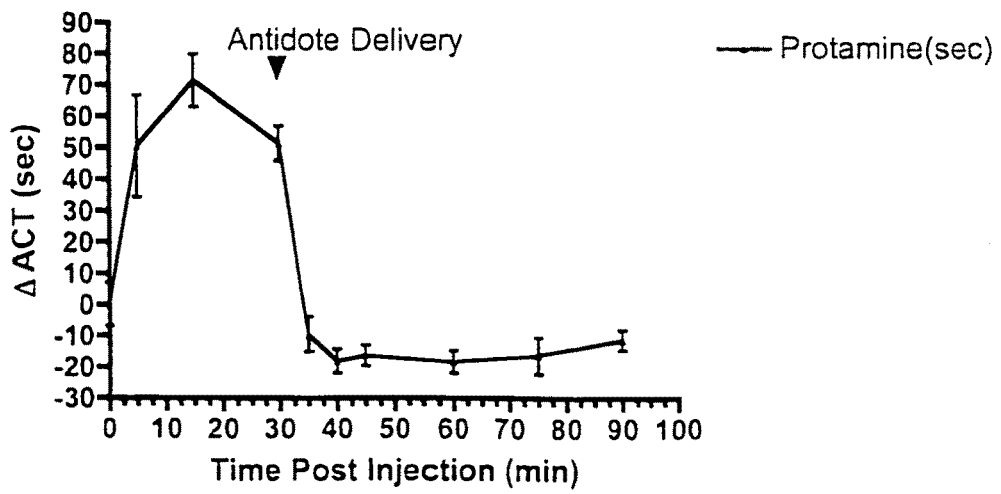
Figure 4C:
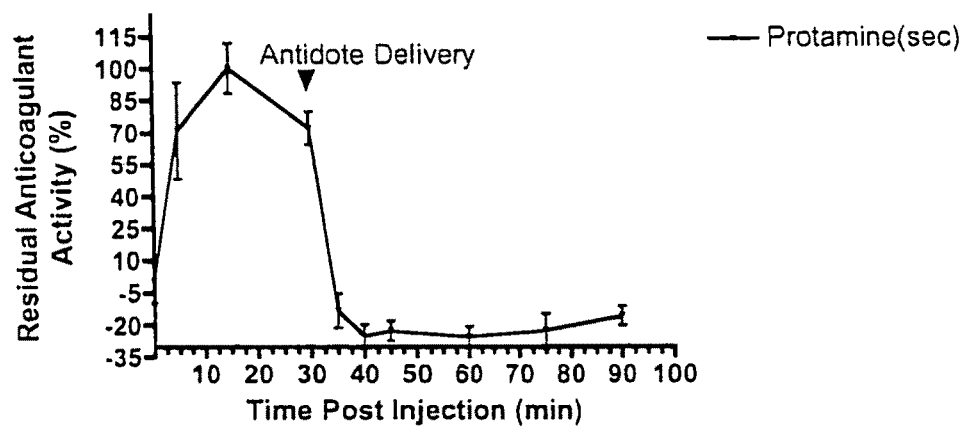

Immediate anticoagulation and prompt reversal is necessary during several cardiovascular procedures, the most common being cardiopulmonary bypass (CPB), as employed during coronary artery bypass grafting (CABG). Without potent anticoagulation, blood clots would form and blood would not circulate in an extracorporeal circuit. However, following the procedure, these values must return to pretreatment levels to prevent massive hemorrhage from the surgical site. After successfully determining the ability of protamine to reverse the activity of the Factor IXa and Factor Xa aptamers for at least 60 minutes in vitro using APTT, the ability of protamine to reverse aptamer anticoagulation in vivo was examined. As shown in FIG. 4A, pigs were successfully anticoagulated with 0.5 mg/kg of the Factor IXa aptamer, as demonstrated by an immediate increase in the ACT from 105 s. to approximately 170 s. When no antidote was administered, the level of anticoagulation gradually decreased in accordance with the 90-minute half-life of the molecule (Rusconi et al, Nat. Biotechnol. 22(1):1423-1428 (2004)). However, following administration of 10 mg/kg of protamine (approx. 40 mg per animal), clotting times as measured by ACT quickly returned to pretreatment baseline levels within five minutes, indicating complete reversal of anticoagulation (FIG. 4B). In addition, this reversal was sustained for the duration of the experiment (at least one hour); all ACT values attained post reversal are below the level needed for adequate anticoagulation (FIG. 4C). Therefore, a bolus injection of the Factor IXa aptamer resulted in immediate anticoagulation that was successfully reversed with protamine.

EXAMPLE V

In order to reverse the aptamer function, an antidote has to be able to compete with the target protein by binding to the aptamer with high affinity. Binding affinities of aptamer 9.3t with a number of polymers and polycationic molecules have been studied by isothermal titration calorimetry (ITC). In the measurements, UA solution was titrated into the aptamer 9.3t by a computer-controlled microsyringe at 298K in PBS. Binding constants and some thermodynamic parameters are summarized in Table 3. Among the chosen polymers, PAMAM dendrimer, PPA-DPA 30k and PLL demonstrated significant affinity with aptamer 9.3t; whereas, the binding constant of aptamer 9.3t to PPA-DPA 8k is much lower, at $8.47 \times 10^5$ M$^{-1}$. No significant binding was observed for the natural polyamines, spermine and spermidine. These results are consistent with the in vitro and in vivo studies which showed that having a strong affinity towards aptamers is a primary criterion as a UA.

TABLE 3

| Host | Potential Antidotes | Binding constant (M$^{-1}$) | ΔG (kJ mol$^{-1}$) | ΔH (kJ mol$^{-1}$) | TΔS (kJ mol$^{-1}$) |
|---|---|---|---|---|---|
| Aptamer Ch-9.3t | Polybrene | $1.6 \times 10^5$ | −29.6 | +71.3 | +101.0 |
| | PAMAM | $1.7 \times 10^6$ | −35.5 | −198.5 | +163.0 |
| | Spermine | $8.8 \times 10^3$ | −22.5 | −1.18 | +21.3 |
| | PPA-DPA 8k | $2.7 \times 10^5$ | −31.0 | +24.7 | +55.7 |
| | PPA-DPA 30k | $1.3 \times 10^7$ | −40.5 | +138.24 | +178.8 |

The isothermal calorimetry measurements (ITC) were conducted by using a thermostatic and fully computer-operated MCS-ITC calorimeter from MicroCal, LLC. Aliquots of 10 μL were titrated into the calorimetric cell every 5 min over a 2 hours period at 298K. A blank run was carried out for each system studied where the titrant was titrated into a cell containing only PBS to allow corrections for the heat effects due to dilution to be made. Data analysis was performed using the customized ITC module of the Origin 5.0 software package and a least squares fitting procedure to fit the data to the appropriate binding model.

EXAMPLE VI

Experimental Details

Clotting Assays

Activated partial thromboplastin time (APTT) assays were performed using a model ST4 mechanical coagulometer (Diagnostica Stago Inc.). Pooled normal human plasma (50 μl) (George King Biomedical) was incubated at 37° C. for 5 min followed by the addition of platelin reagent (50 μl) (Trinity Biotech) and aptamer (in wash buffer) (5 μl) or wash buffer alone, and incubated for 5 min at 37° C. Antidote molecule or buffer (5 μl) was than added and incubated at 37° C. for 5 min followed by the addition of 25 mM CaCl$_2$ (50 μl) to initiate the clotting reaction (Rusconi et al, Nature 419:90 (2002)). Data is shown as the change in clot time. All reactions were performed in triplicate.

Platelet Function Assays

The Platelet Function Analyzer, PFA-100 (Dade Behring, Deerfield, Ill.), measures platelet function in terms of clot formation time. In this assay, collagen/ADP cartridges were used to activate the platelets. 800 μl of whole blood was mixed with aptamer in platelet binding buffer (40 μl) (150 mM NaCl; 20 mM Hepes pH: 7.4; 5 mM KCl; 1 mM MgCl$_2$ and 1 mM CaCl$_2$) and incubated for 5 min at room temperature. Antidote molecule or platelet buffer (40 μl) was than added and incubated for 5 min at room temperature. This mixture was then added to a collagen/ADP cartridge and tested for its closing time (Harrison, Blood Rev. 19:111 (2005)). The maximum closing time of the PFA-100 is 300 seconds. Data is shown as the change in closing time. All reactions were performed in triplicate.

Isothermal Calorimetry

The isothermal calorimetry measurements (ITC) were conducted by using a thermostatic and fully computer-operated MCS-ITC calorimeter from MicroCal, LLC. Aliquots of 10 μl were titrated into the calorimetric cell every 5 min over a 2 hour period at 298K. A blank run was carried out for each system studied where the titrant was titrated into a cell containing only PBS to allow corrections for the heat effects due to dilution to be made. Data analysis was performed using the customized ITC module of the Origin 5.0 software package and a least squares fitting procedure to fit the data to the two-sites binding model.

In Vitro Assessment of CDP/9.3t Interaction by Gel Electrophoresis and Dynamic Light Scattering (DLS)

Gel electrophoresis was performed by adding 5 μl volume of 0.01 mg/mL 9.3t in 1×PBS, an equal volume of CDP in 1×PBS. This was performed six times in parallel using CDP solutions of various concentrations to give resulting solutions having CDP/9.3t ratios (w/w) of 0/1 (lane 2), 2/1 (lane 3), 4/1 (lane 4), 6/1 (lane 5), 8/1 (lane 6), and 10/1 (lane 7). To each of these 10 μl solutions, 2 μl of nucleic acid loading buffer was added, and 10 μl of each resulting solution was loaded per well of a 15% polyacrylamide/TBE gel and electrophoresed (1 h, 100 V). The gel was then incubated in 1×TBE buffer containing 0.5 μg/mL ethidium bromide for 30 min and visualized. CDP alone (0.0335 mg/mL in 1×PBS), 9.3t alone (0.005 mg/mL in 1×PBS), and CDP/9.3t (0.0335 mg/mL CDP, 0.005 mg/mL 9.3t; 6.7/1 w/w in 1×PBS) were analyzed by dynamic light scattering (DLS) using a ZetaPALS particle size analyzer. Three consecutive 3-minute runs were performed for each sample; the effective diameter and average particle count rate were determined.

Analysis of CDP-Im-siRNA Complex Formation In Vivo.

Four female BALB/c mice received a single tail-vein injection of naked, non-chemically-modified siRNA. One minute after this injection, two of the mice received a separate tail-vein injection of CDP-Im along with two other typical nanoparticle components, AD-PEG and AD-PEG-Tf (Heidel et al, Proc. Natl. Acad. Sci. USA 104:5715 (2007)). Two minutes later, blood was collected from all mice and centrifuged to separate serum. Serum samples were then electrophoresed using a 156 TBE polyacrylamide gel and visualized using ethidium bromide.

Swine Systemic Anticoagulation and Reversal Study

Swine (2.5-3.5 kg) were randomly assigned to treatment groups. For all groups, anesthesia was induced by intramuscular injection of ketamine (22 mg/kg) and acepromazine (1.1 mg/kg). A catheter was then placed in the ear vein, through which anesthesia was maintained with fentanyl, first with a 100 μg/kg bolus, and then with a continuous infusion of 60 $\mu g \cdot kg^{-1} \cdot h^{-1}$. The swine were then intubated and mechanically ventilated. Following placement of the esophageal or rectal temperature probe and $SP0_2$ monitor, the femoral artery and vein were cannulated. The arterial line was used as a means to continuously monitor mean arterial blood pressure and heart rate, as well as removal of blood samples for evaluation of ACT. After determining baseline ACT values, the venous line was used to administer the Factor IXa aptamer (0.5 mg/kg). Blood samples were then drawn from the arterial line at 5, 15, and 30 minutes post aptamer administration. The ACT values were measured by using Hemochron Jr. Signature Microcoagulation System (ITC, Edison N.J.). For experiments involving antidote administration, 40 mg protamine (10 mg/mL) or 10 mg CDP (10 mg/ml) was given over five minutes via the femoral vein catheter at 30 minutes post aptamer injection. For all animals, subsequent blood samples were at taken at 35, 40, 55, 60, 75, and 90 minutes post aptamer administration. All data points are done in duplicate per animal. At the closure of the experiment, swine were euthanized with Euthasol (175 mg/kg) via femoral vein.

All animals received humane treatment in accordance with the *Guide for the Care and Use of Laboratory Animals* published by the National Institutes of Health, as approved by the Duke University Animal Care and Use Committee.

Results

Figure 5A:
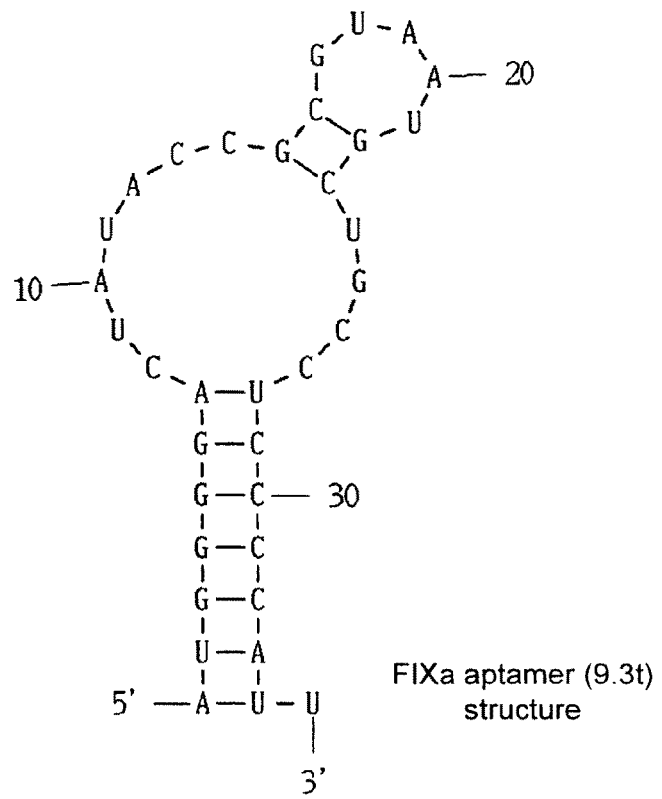
FIGS. 5A-5E: Structures of aptamers used and protamine mediated reversal of anticoagulant aptamer activity.
Figure 5A:
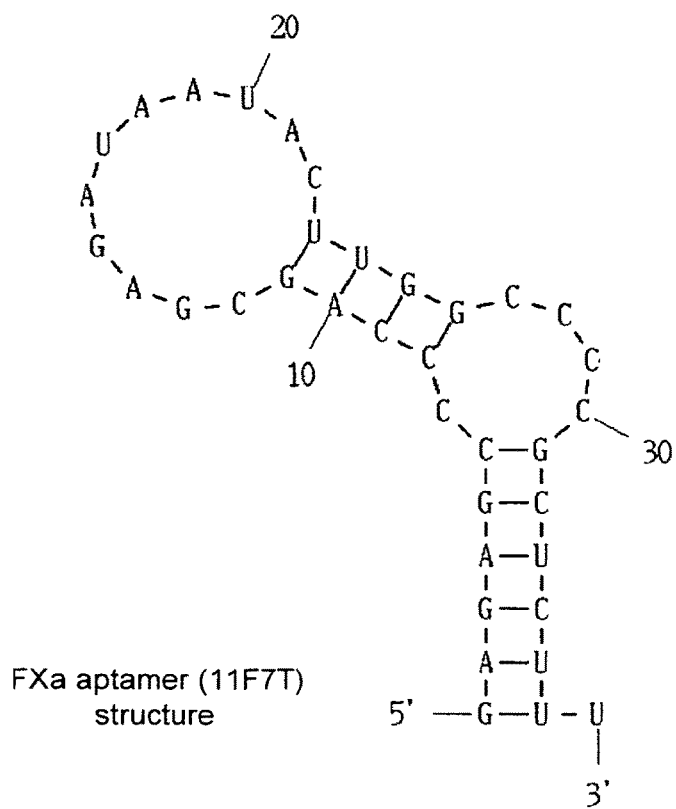
Figure 5A:
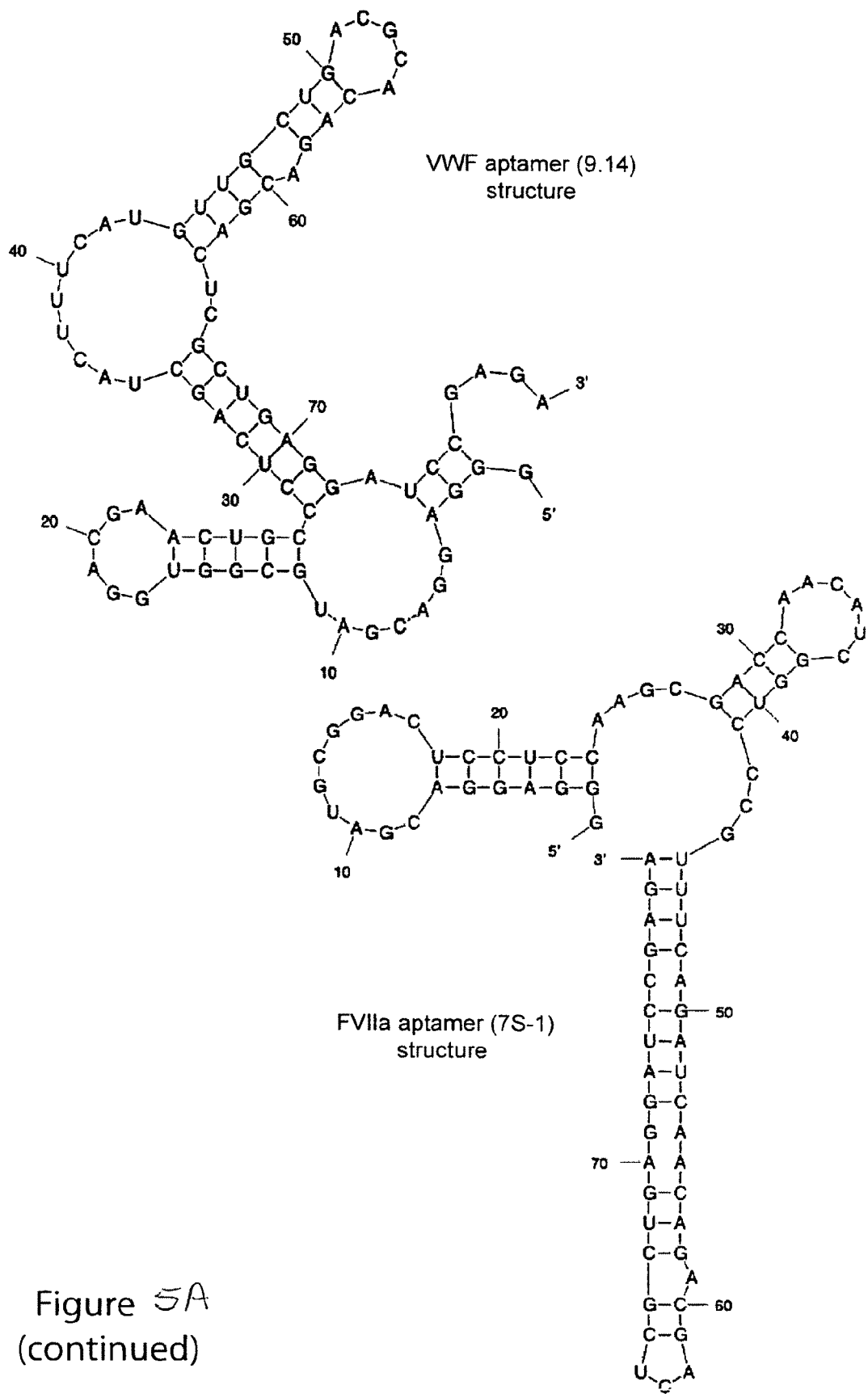
Figure 5A:
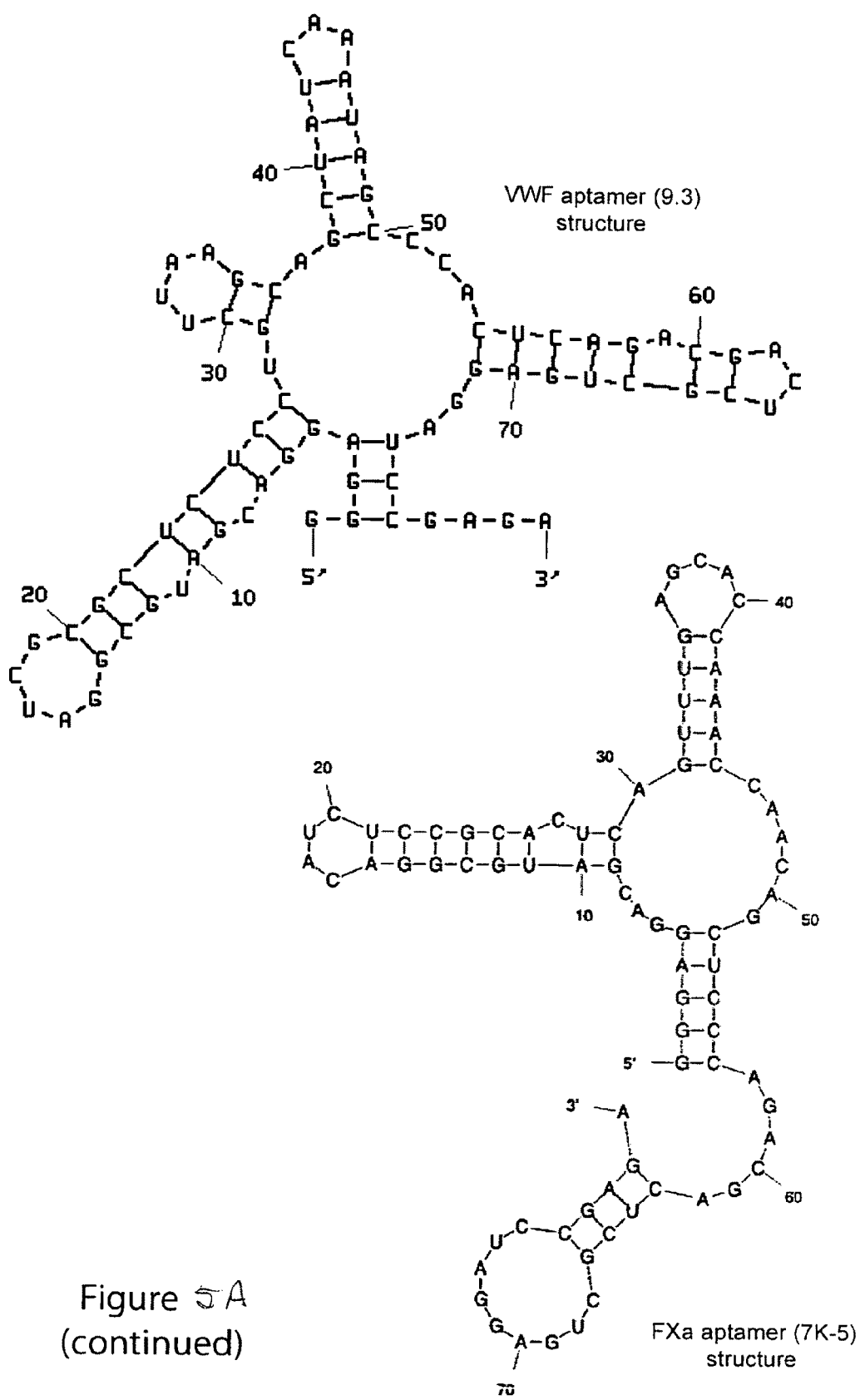

Two aptamers selected to different targets (thrombin and VEGF) have been shown to interact with the heparin binding domain (HBD) on their target proteins (Lee et al, Proc. Natl. Acad. Sci. USA 102:18902 (2005), White et al, Mol. Ther. 4:567 (2001)). An initial investigation was made as to whether protamine, the antidote for heparin, could reverse the activity of two aptamers that target coagulation factors IXa (aptamer 9.3t) and Xa (aptamer 11F7T). The activated partial thromboplastin time (APTT) assay is used for diagnosing coagulation factor anomalies and also for monitoring anticoagulation therapy. It has been demonstrated previously that the APTT assay could be utilized to monitor the anticoagulant effects of both FIXa and FXa aptamers (Rusconi et al, Nature 419:90 (2002), Rusconi et al, Nat. Biotechnol. 22:1423 (2004)) (unpublished results). These aptamers have significantly different primary sequences and secondary structures (as predicted by mFold, FIG. 5A) (Zuker, Nucleic Acids Res. 31:3406 (2003)) and target different proteins in the coagulation cascade. As shown in FIG. 5B, aptamer 9.3t is a potent anticoagulant. However, addition of protamine neutralized the anticoagulant effects of this aptamer within 5 minutes (FIG. 5B). Similarly, aptamer 11F7T is a potent anticoagulant agent and protamine can also neutralize the activity of this aptamer (FIG. 5C). In both cases, 2.5 μg of protamine was able to totally reverse the aptamers' activity in an APTT clotting assay (FIG. 5D) at a 2 fold lower concentration than is routinely used to reverse heparin's anticoagulant activity. Moreover, protamine was able to reverse the anticoagulant activity of the two aptamers simultaneously (FIG. 5E) and such reversal was maintained for at least an hour.

Figure 6:
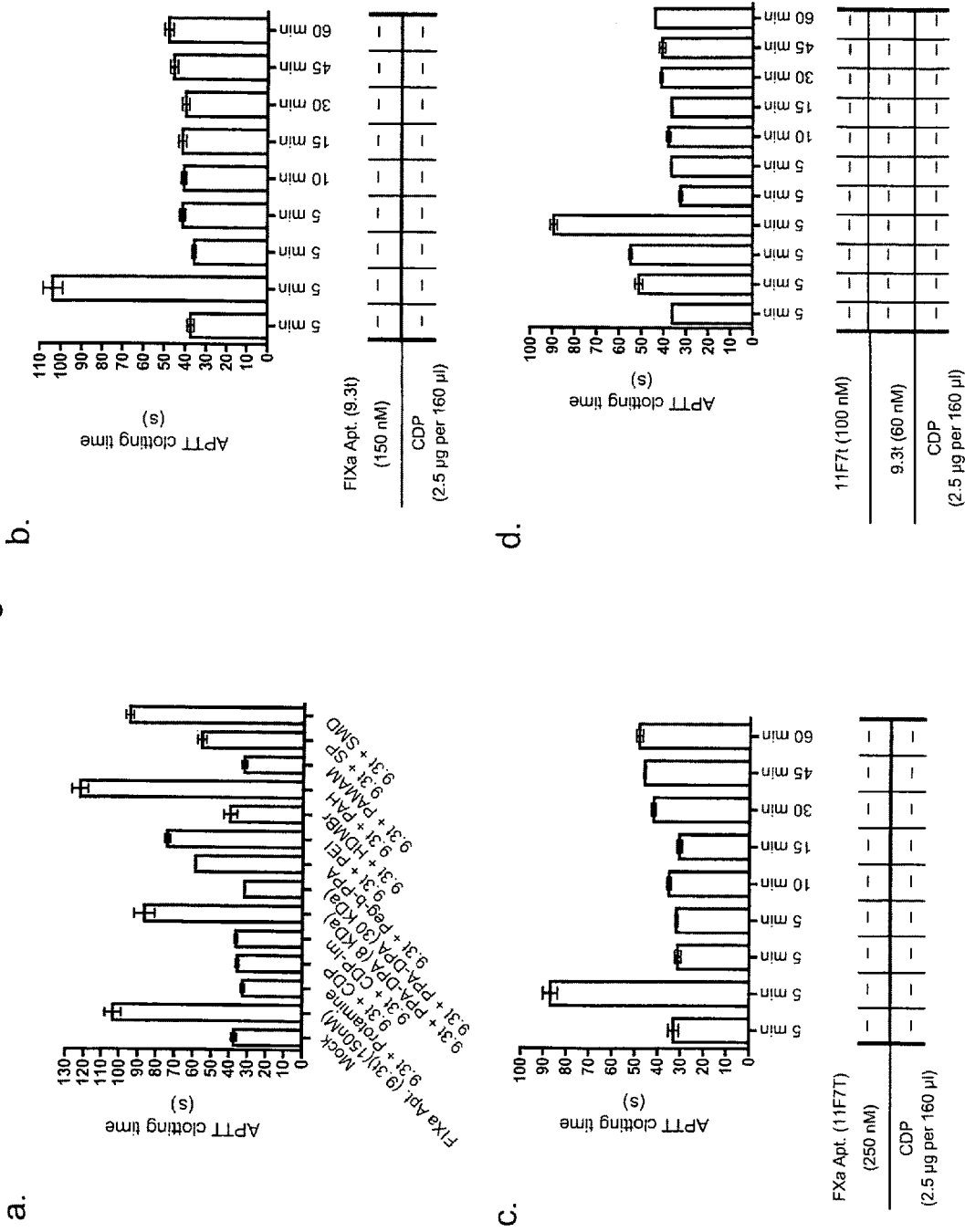
FIGS. 6A-6F: Polymer mediated reversal of anticoagulant aptamer activity.
Figure 6:
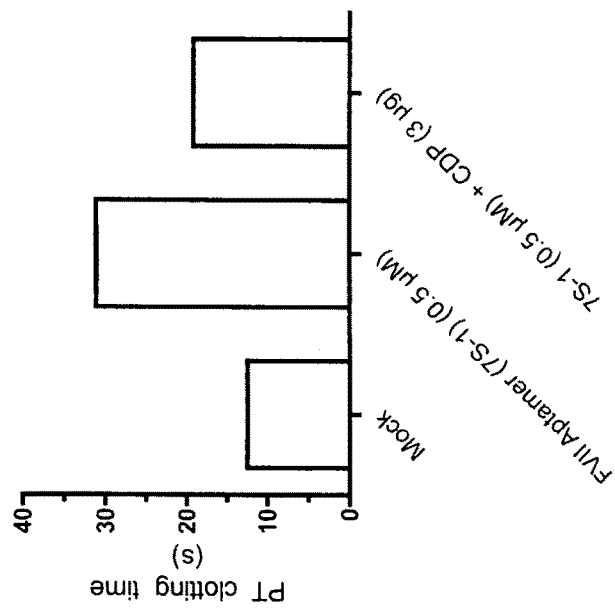
Figure 6:
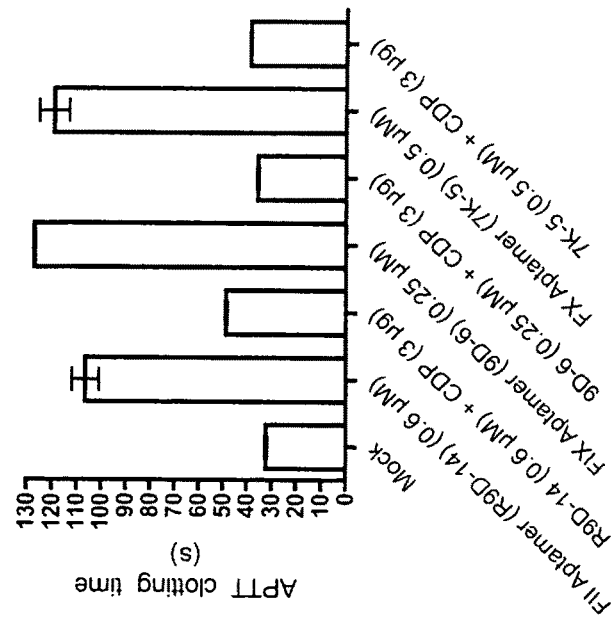
Figure 7:
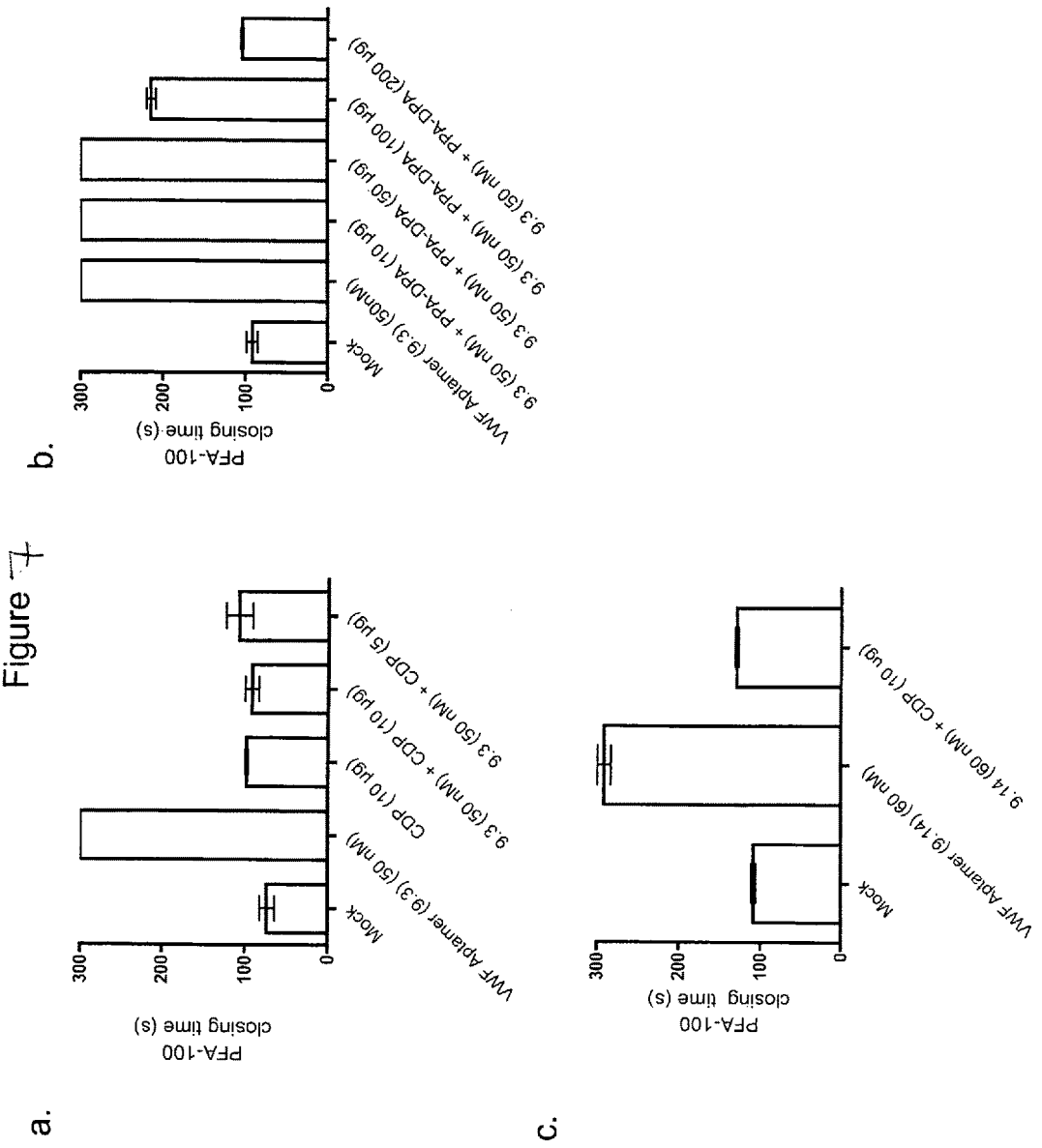

Although protamine is routinely used to reverse the activity of heparin following cardiopulmonary bypass surgery, protamine administration is associated with several side effects, including increased pulmonary artery pressure, decreased systolic and diastolic blood pressure, impaired myocardial oxygen consumption, and reduced cardiac output, heart rate, and systemic vascular resistance (Nimjee et al, Mol. Ther. 14:408 (2006), Hird et al, Circulation 92:II1433 (1995), Porsche et al, Heart Lung 28:418 (1999), Shigeta et al, J. Thorac. Cardiovasc. Surg. 118:354 (1999), Welsby et al, Anesthesiology 102:308 (2005)). Therefore, the decision was made to identify other agents that could rapidly reverse the activity of aptamers. A number of nucleic acid binding polymers were screened for their ability to act as antidotes for aptamer 9.3t (Table 4). As shown in FIG. 6A, several of the polymers were able to completely reverse the activity of the aptamer completely within 5 minutes. To better understand why certain polymers were more effective than others, the interactions of the different polymers with aptamer 9.3t were measured by isothermal titration calorimetry (ITC). A two-site model was used to interpret the ITC data for the interactions between the cationic polymers and aptamer 9.3t. Binding constants and some thermodynamic parameters are summarized in Table 5. All the interactions are entropy driven (as expected) except for with PAMAM, and most are also enthalpy driven. Although no conclusions can be drawn about the mechanisms of the interactions, the trends of binding strength, in the two-site model, are consistent with the results from the APTT screening. Protamine, CDP, CDP-Im, PPA-DPA and PAMAM demonstrated significant and similar affinities for aptamer 9.3t; whereas the binding constants of polybrene and spermine are orders of magnitude lower. Thus, a direct correlation exists between the polymer's affinity for the aptamer and its potency as an antidote.

Since CDP has high binding affinity for the aptamer and is known to have a low toxicity, this polymer was tested in time course experiments (Gonzalez et al, Bioconjug. Chem. 10:1068 (1999)). Similar to protamine, CDP could rapidly and durably reverse the activity of these two distinct anticoagulant aptamers (9.3t and 11F7T) in vitro (FIGS. 6B-6D). Next, an examination was made of CDP's ability to reverse the activity of four additional aptamers that target factors II, IX, X and VII. As shown in FIGS. 6E and 6F, CDP can rapidly reverse the activity of each of these aptamers.

TABLE 4

Definitions and molecular structures of the selected potential antidote.

| Polymer | Abbreviation | Molecular structure |
|---|---|---|
| β-cyclodextrin-containing polycation | CDP | |

TABLE 4-continued

Definitions and molecular structures of the selected potential antidote.

| Polymer | Abbreviation | Molecular structure |
| --- | --- | --- |
| β-cyclodextrin-containing polycation (imidazole-containing variant) | CDP-Im | *(chemical structures of CDP-Im shown)* |
| Polyphosphoramidate polymer (8kDa, 30kDa) | PPA-DPA 8k, PPA-DPA 30k | *(chemical structure shown)* |
| Polyamidoamine dendrimer, 1,4-diaminobutane core, G3 | PAMAM | [NH$_2$—(CH$_2$)$_4$—NH$_2$]:(G = 3); dendri PAMAM(NH$_2$)$_{32}$ |

TABLE 4-continued

Definitions and molecular structures of the selected potential antidote.

| Polymer | Abbreviation | Molecular structure |
|---|---|---|
| Polybrene | | $-\left(N^{\oplus}(CH_3)_2-(CH_2)_3-N^{\oplus}(CH_3)_2-(CH_2)_6\right)_n \cdot 2\,Br^{\ominus}$ |
| Spermine | | $NH_2-(CH_2)_3-NH-(CH_2)_4-NH-(CH_2)_3-NH_2$ |

TABLE 5

Binding constants and thermodynamic parameters of (a) the first stage binding and (b) the second stage binding, between the selected potential antidotes and aptamer 9.3t.

a.

| Polymer | K1 (M$^{-1}$) | ΔG (kJ mol$^{-1}$) | ΔH (kJ mol$^{-1}$) | TΔS (kJ mol$^{-1}$ K) |
|---|---|---|---|---|
| protamine | 3.09E+07 | −42.73 | −37.57 | 5.16 |
| CDP | 2.63E+07 | −42.33 | −27.93 | 14.41 |
| CDP-lm | 3.69E+08 | −48.87 | −44.52 | 4.35 |
| PPA 30k | 6.71E+08 | −50.35 | 100.58 | 150.94 |
| PPA 8K | 2.46E+07 | −42.16 | 24.84 | 67.00 |
| PAMAM | 7.37E+08 | −50.59 | −225.22 | −174.64 |
| polybrene | 9.23E+06 | −39.74 | 63.60 | 103.33 |
| spermine | 1.63E+06 | −35.43 | −1.01 | 34.42 | b.

| Polymer | K2 (M$^{-1}$) | ΔG (kJ mol$^{-1}$) | ΔH (kJ mol$^{-1}$) | TΔS (kJ mol$^{-1}$ K) |
|---|---|---|---|---|
| CDP | 1.20E+07 | −40.39 | −6.89 | 33.50 |
| CDP-lm | 4.54E+07 | −43.68 | −26.85 | 16.83 |
| PPA 30k | 1.03E+07 | −40.00 | 134.93 | 174.94 |
| PPA 8K | 2.28E+06 | −36.27 | 4.20 | 40.47 |
| PAMAM | 3.69E+07 | −43.17 | −68.24 | −25.07 |
| polybrene | 8.03E+05 | −33.68 | 3.04 | 36.72 |
| spermine | 1.26E+05 | −29.10 | −0.30 | 28.80 |

Figure 7A:
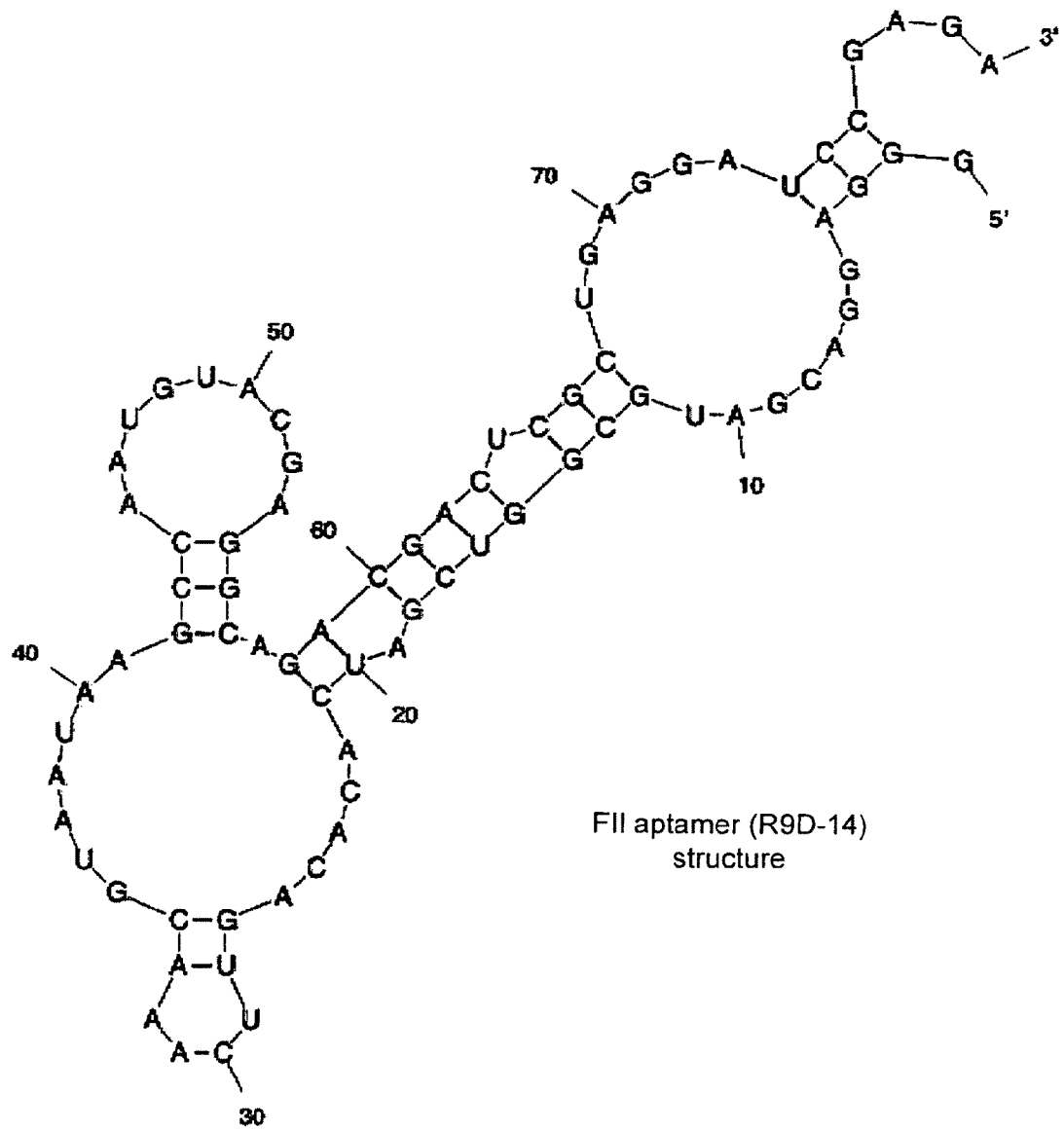
FIGS. 7A-7C: Polymer mediated reversal of antiplatelet aptamer function.
Figure 5A:
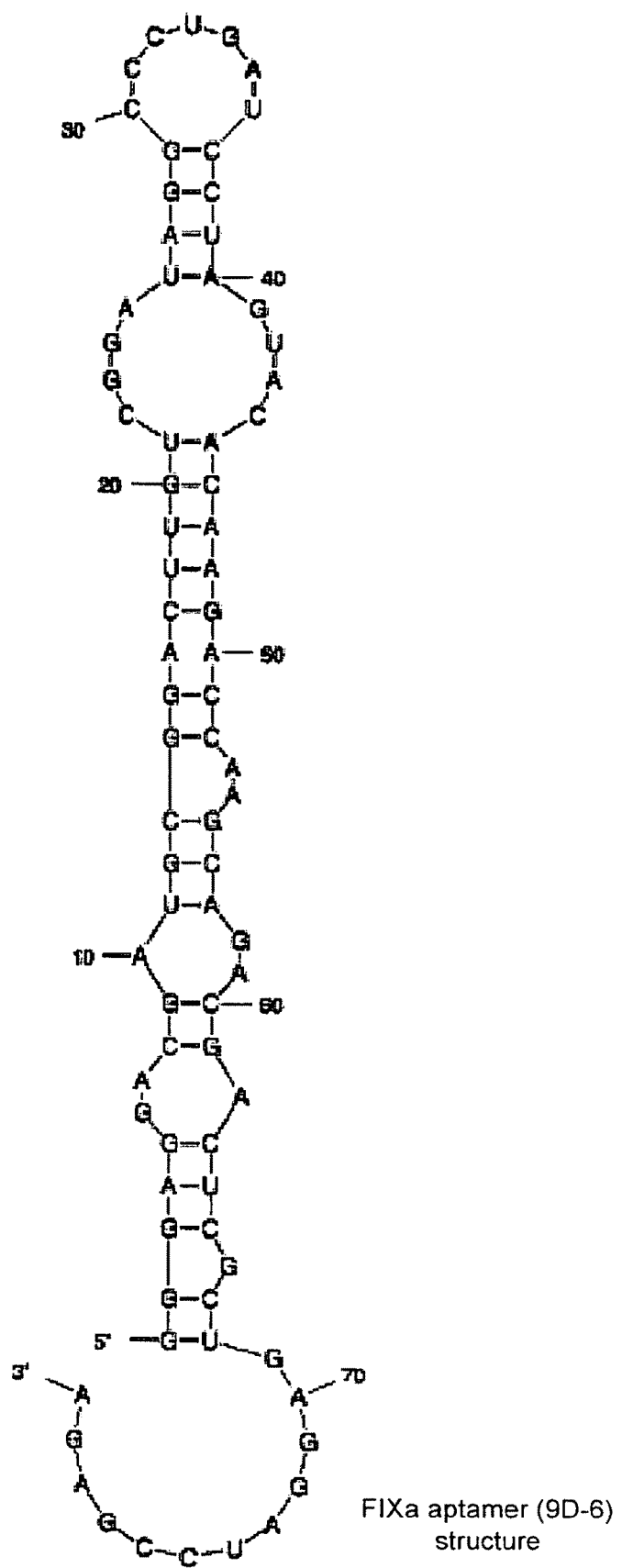
Figure 5:
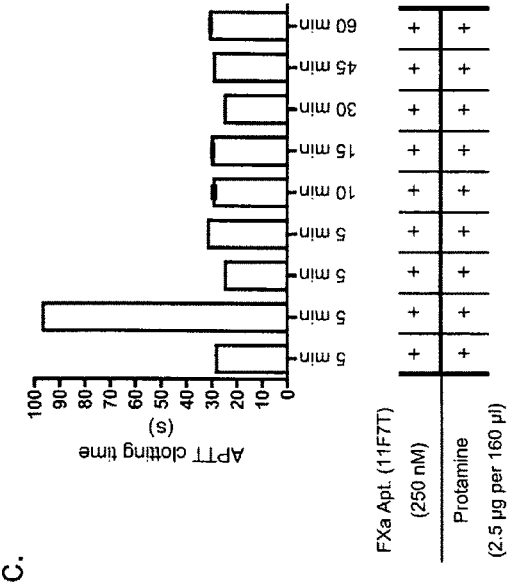
Figure 5:
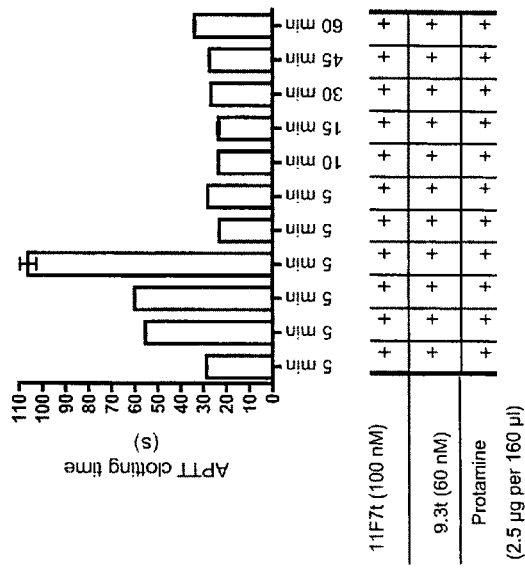
Figure 5:
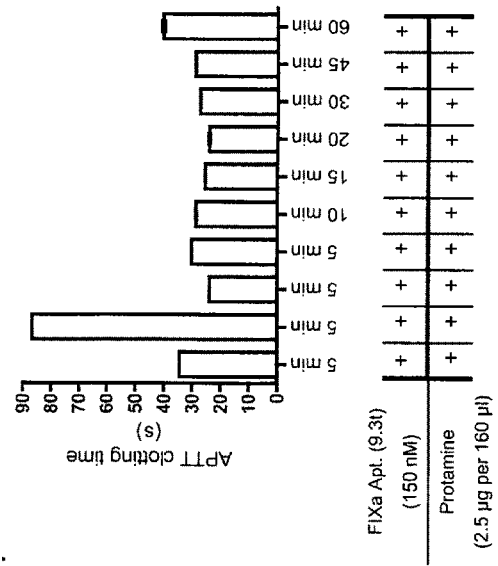
Figure 5:
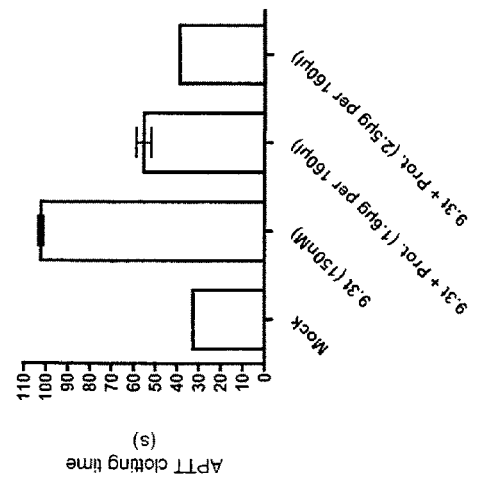

CDP and PPA-DPA were next tested for their ability to neutralize the antiplatelet effects of VWF aptamer 9.3 and VWF aptamer 9.14 (FIG. 5A) in a platelet function assay (PFA-100) (Oney et al, Oligonucleotides 17:265 (2007)). VWF aptamers 9.3 and 9.14 have no sequence or structural similarity to the previously tested aptamers and both can inhibit platelet function in while blood (FIGS. 7A and 7B). Addition of either CDP or PPA-DPA and resulted in rapid reversal of VWF aptamer 9.3 antiplatelet activity (FIGS. 7A and 7B) with CDP achieving complete reversal at an order of magnitude lower amount than PPA-DPA. Moreover, CDP was able to rapidly reverse the activity of VWF aptamer 9.14 at this same concentration (FIG. 7C). These experiments further demonstrate that CDP and PPA-DPA can act as sequence-independent antidotes for aptamers. Furthermore, these results point to the broad applicability of this approach since the antidotes work in both plasma and whole blood against eight different aptamers.

Figure 8:
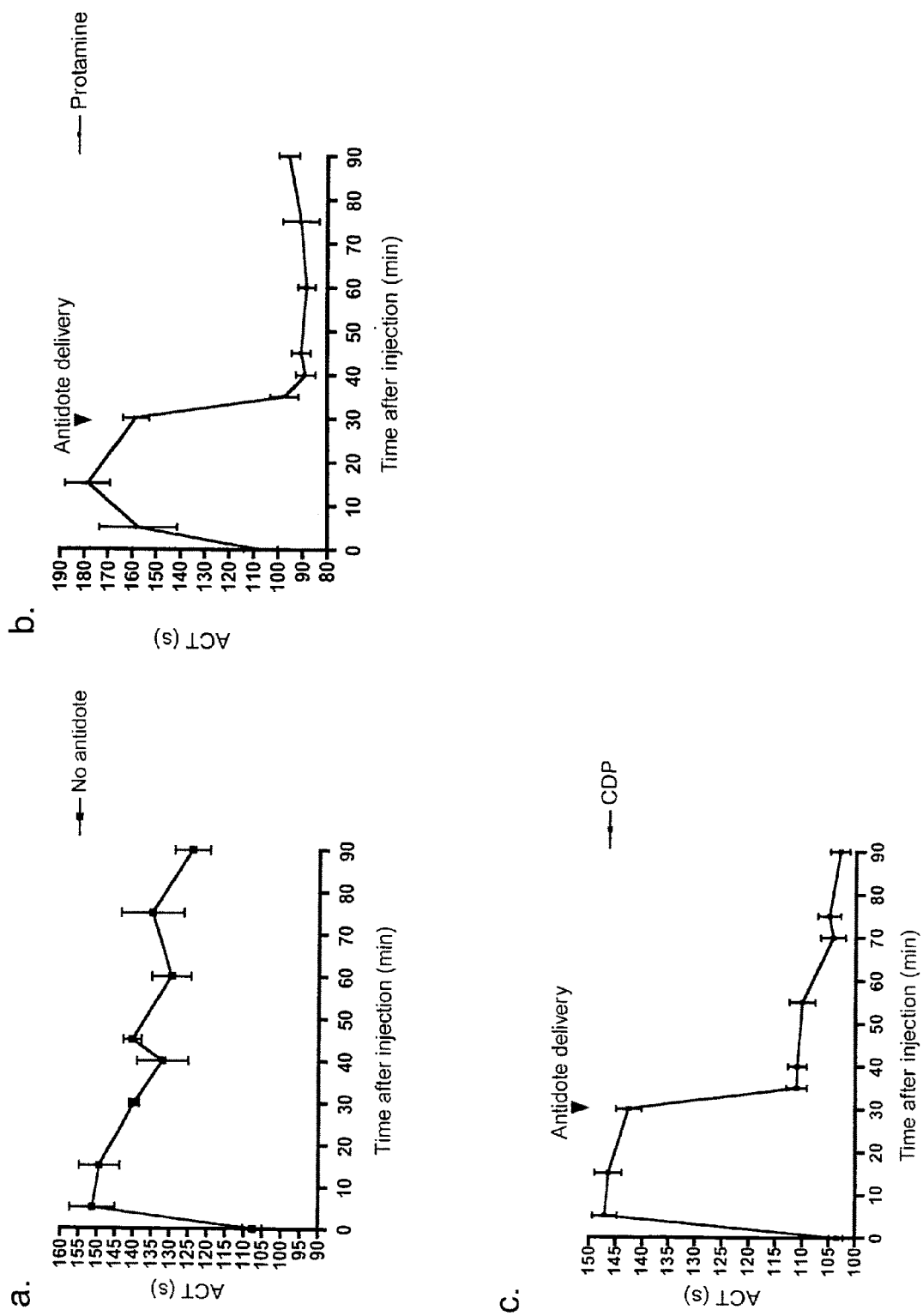
FIGS. 8A-8C: In vivo aptamer and antidote activity.
Figure 9:
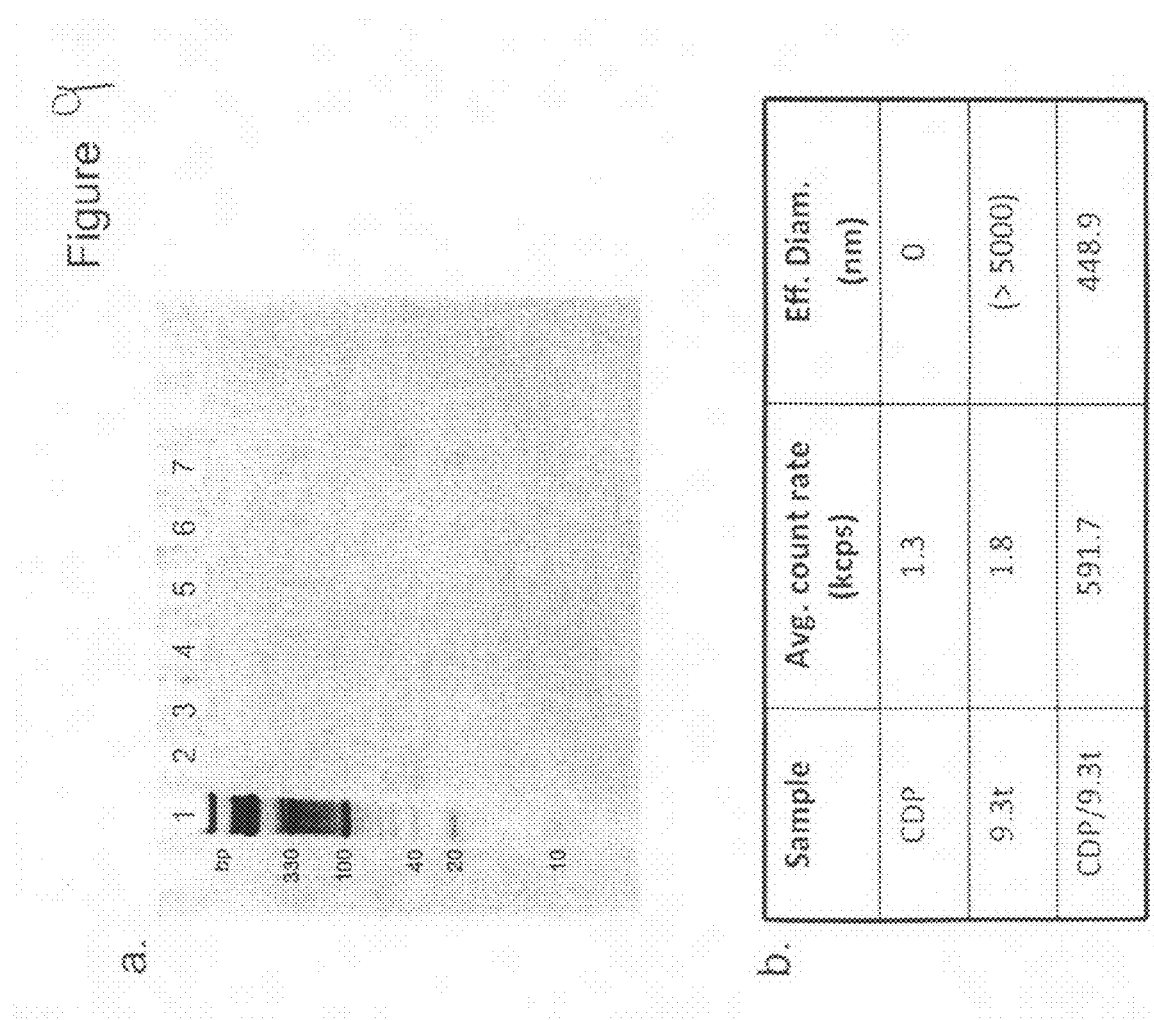
FIGS. 9A-9B: In vitro characterization of CDP and aptamer 9.3t interaction.
Figure 10:
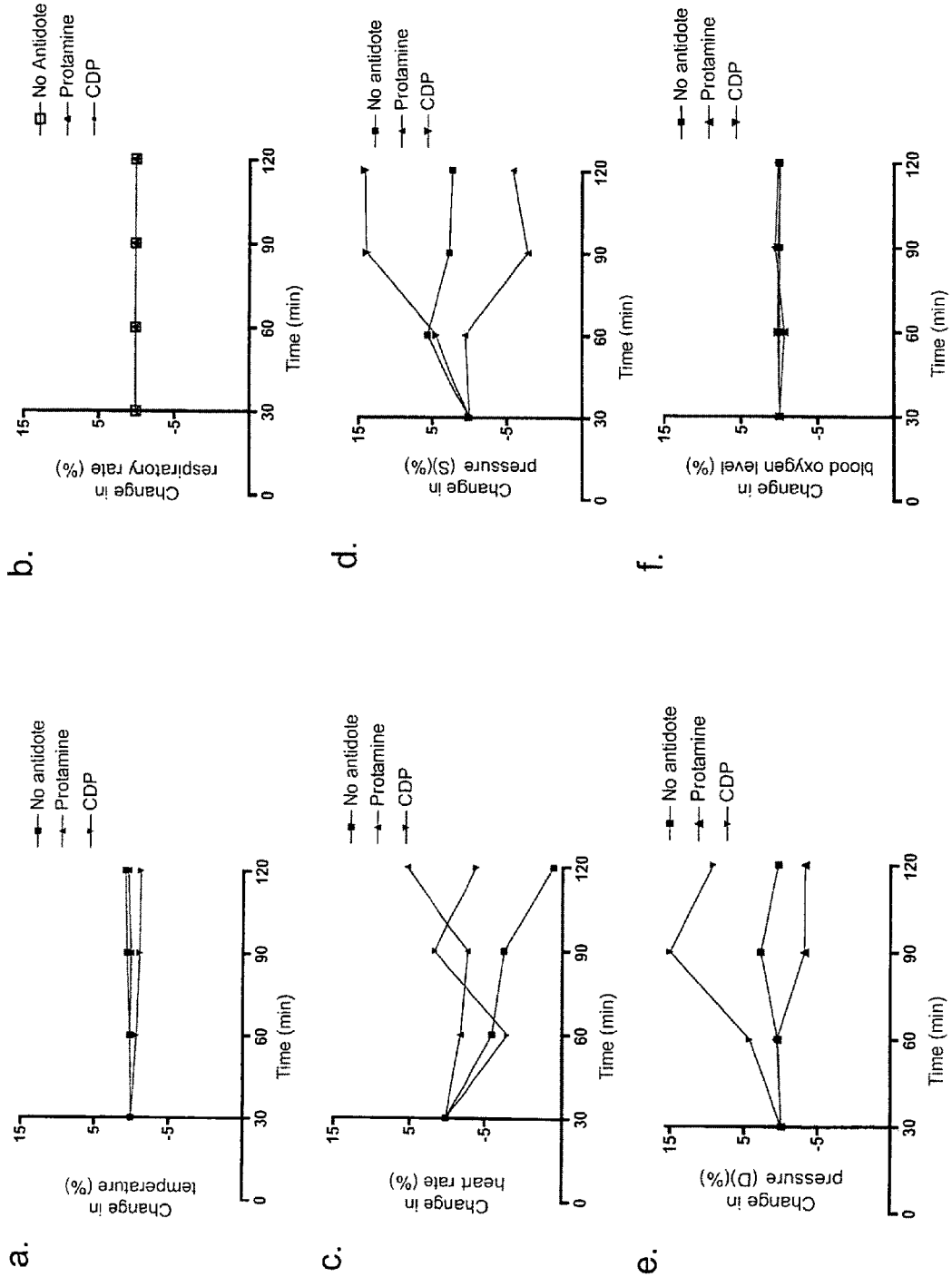
FIGS. 10A-10F: The vital signs of the animals during the anticoagulation experiments compared to pre-antidote injection state.
Figure 11:
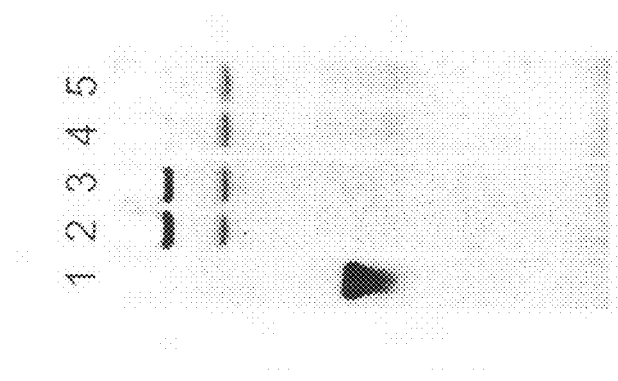
FIG. 11: Evidence for association of CDP-im with siRNA in vivo. Gel electrophoresis was performed on serum samples from mice that received a single injection of naked, non-chemically-modified siRNA (fourth and fifth lanes from left) or that received consecutive injections of naked siRNA followed by a CDP-Im-containing solution administered one (1) minute apart (second and third lanes from left). The first lane contains the siRNA stock solution for reference. All four serum-containing samples produced a distinct band slightly below the wells that is the result of non-specific interaction between the ethidium bromide (used for siRNA detection) and serum components. The fourth and fifth lanes show no evidence for siRNA remaining in the wells and bands that co-migrate with the siRNA control (first lane), as expected. In contrast, the second and third lanes show strong siRNA-containing bands in the wells and no evidence for siRNA migration through the gel. Such bands in the wells were not seen when the CDP-Im-containing solution was administered alone (data not shown) and are indicative of siRNA interaction with CDP-Im within the mouse bloodstream.

Next, studies were undertaken to determine whether such UAs were able to reverse aptamer activity in vivo. Results from in vitro experiments (gel electrophoresis and dynamic light scattering) using the same concentrations as anticipated for use in animals demonstrated that CDP is able to bind to the aptamer and form a composite entity (FIG. 9) and it was observed that CDP-Im formed a complex with siRNA when sequentially injected into mice (FIG. 11). Therefore, the activity of the UAs was evaluated in a swine anticoagulation model. As seen in FIG. 8A, pigs (n=5) were anticoagulated by the FIXa aptamer (Ch-9.3t) (0.5 mg/kg) that had been modified with a cholesterol at its 5' end to improve its circulating half life (Rusconi et al, Nat. Biotechnol. 22:1423 (2004)). An immediate increase was observed in the activated clotting time (ACT) (from 105+/−5 seconds to 150+/−5 seconds) for the treated animals. When no antidote was administered, the level of anticoagulation only gradually decreased over the 90 minute time frame of the experiment (FIG. 8A). However, administration of protamine (10 mg/kg) resulted in a total reversal of the anticoagulant effect within five minutes (n=5) (FIG. 8B). In addition, this reversal was sustained for the remainder of the experiment, 60 minutes (FIG. 8B). Similarly, CDP (n=5) (2.5 mg/kg) was also able to rapidly and durably reverse the activity of this aptamer in vivo (FIG. 8C). Furthermore, no toxicities were observed following administration of these antidotes during the experiment (FIG. 10). All vital signs stayed within error of their base line levels with the exception that protamine induced a mild hypotension and CDP a mild hypertension (<15% change; FIGS. 10D and 10E). These results demonstrate that both protamine and CDP can act as antidotes for aptamers in vivo.

Between 1998 and 2005, the number of serious adverse drugs events reported to the FDA increased 2.6-fold, and fatal adverse events increased 2.7-fold to 15,107 events in 2005 (Moore et al, Arch. Intern. Med. 167:1752 (2007); Lazarou et al, JAMA 279:1200 (1998)). Therefore, a pressing medical need exists to develop safer and more controllable therapeutic strategies. Unfortunately, it has been both technically challenging and cost prohibitive to develop antidote molecules to counteract the side effects of most medicines. However, characteristics unique to oligonucleotides can be used to design UAs that can sequester aptamers and reverse their activity regardless of the aptamer's primary sequence and folded structure. Initial studies demonstrated that protamine, a commonly used and inexpensive heparin reversal agent with well known side effects can be utilized as an antidote for multiple aptamers (Carr et al, J. Cardiovasc. Surg. (Torino) 40:659 (1999), Stanker et al, Mol. Immunol. 30:1633 (1993)). Furthermore, the observation that protamine can neutralize aptamer activity indicates that protamine should be used with caution in patients being treated with oligonucleotide-based drugs since protamine may unintentionally reverse the activity.

In the quest to find UAs with more favorable characteristics, such as low toxicity, a number of polymeric gene carriers were tested for their ability to reverse the activity of aptamers. The field of nonviral gene therapy has stimulated the synthesis of many polymers for the delivery of plasmid DNA and siRNA. Rigidity, hydrophobicity/hydrophilicity, charge density, biodegradability, and molecular weight of the polymer chain are all parameters that can be adjusted to achieve an optimal complexation with oligonucleotides (Davis et al, Curr. Med. Chem. 11:179 (2004), Mao and Leong, Adv. Genet. 53:275 (2005)). Moreover, Joachimi et al. demonstrated that a small cationic porphyrin could act as an antidote to a G-quartet containing thrombin aptamer (Joachimi et al, J. Am. Chem. Soc. 129:3036 (2007)). Therefore, in the study described herein, a number of DNA or siRNA delivery polymers were screened. It was demonstrated that several of them can reverse the activity of multiple aptamers in vitro and that CDP can also rapidly reverse the activity of an anticoagulant aptamer in large animals.

Previously, a strategy was developed to reverse the activity of aptamers using Watson-Crick base pairing rules to create a customized antidote oligonucleotide for each aptamer (Rusconi et al, Nature 419:90 (2002), Rusconi et al, Nat. Biotechnol. 22:1423 (2004)). This customization is very costly since for each aptamer a new antidote oligonucleotide has to be developed, tested and manufactured. Another concern with this approach is that when antidote oligonucleotides bind to aptamers, a double stranded RNA is formed. This double stranded RNA complex may stimulate the innate immune system (Kleinman et al, Nature 452:591-597 (2008), Epub 2008 Mar. 26; Schroder and Bourie, Trends Immunol. 26:462 (2005)). Although both the RNA aptamer and the antidote oligonucleotide are often comprised of modified oligonucleotides (i.e. 2'-F and 2'-Ome RNA) a potential danger still exists that these molecules may activate TLR-3 receptors as short 2'Ome siRNA duplexes have been reported to induce such effects (Kleinman et al, Nature 452:591-597 (2008); Epub 2008 Mar. 26). Finally, because most indications will not require an antidote for the reversal of drug action 100% of the time, the added cost of developing a customized antidote is difficult to justify for most drugs that usually are safe but are associated with relatively rare but serious side effects. Thus, it is believed that the UA approach described herein will be more broadly applicable than the previous customized antidote oligonucleotide previously.

As with any new therapeutic agent, the safety of the UA molecules will have to be tested in the clinic. Recent studies evaluating the toxicity of CDP-Im in non-human primates demonstrate that such compounds have a favorable safety profile (Heidel et al, Proc. Natl. Acad. Sci. USA 104:5715 (2007)) leading Calando Pharmaceuticals Inc. to receive FDA approval for a first in human study using this compound to deliver siRNAs in cancer patients. Thus, there is reason to be optimistic that the UA strategy describe herein can be rapidly translated into the clinic.

What is claimed is:

1. A method of inhibiting the activity of a nucleic acid molecule (NAM) that binds to a target molecule and elicits a pharmacological effect, said method comprising contacting said NAM with a universal antidote (UA) under conditions such that said UA binds to said NAM and modifies the interaction between said NAM and said target, wherein said binding of said UA to said NAM is independent of the nucleotide sequence of said NAM and wherein said UA is a pharmaceutically acceptable polycationic polymer selected from the group consisting of PPA-DPA, CDP, CDP-Im, PAMAM, and HDMB.

2. The method according to claim 1 wherein said NAM is an aptamer, a siRNA, a microRNA, a ribozyme or an antagomir.

3. The method according to claim 2 wherein said NAM is an aptamer.

4. The method according to claim 3 wherein said NAM is an aptamer to human factor IXa or human factor Xa.

5. The method according to claim 1 wherein said target molecule is a peptide, protein, glycoprotein, polysaccharide or nucleic acid.

6. The method according to claim 5 wherein said target molecule is an enzyme, hormone, receptor, adhesion molecule, metabolite, or cofactor.

7. The method according to claim 5 wherein said target molecule is factor VIIa, factor IXa, factor Xa, factor XIa, thrombin or protein C.

8. The method according to claim 1 wherein said UA reverses an immune system activating effect of said NAM.

9. The method according to claim 1, wherein said UA reverses an anticoagulant and antithrombic effect of said NAM.

10. The method according to claim 1, wherein said UA reverses an immunosuppressive effect of said NAM.

11. The method according to claim 1, wherein said UA reverses an acetylcholine receptor blocking activity of said NAM.

12. The method according to claim 1 wherein said contacting is effected in vivo.

13. The method according to claim 12 wherein said contacting is effected in a mammal.

14. The method according to claim 13 wherein said mammal is a human.

15. A method of screening for a candidate UA capable of inhibiting the activity of a nucleic acid molecule (NAM) comprising contacting a test compound with a NAM and determining whether said test compound binds to said NAM, wherein a test compound that binds to said NAM in a manner independent of the nucleotide sequence of said NAM is a candidate UA, and wherein said UA binds said NAM with a binding constant greater than $1.0 \times 10^6$ $M^{-1}$.

16. The method according to claim 15 wherein said NAM is an aptamer.

17. The method according to claim 15 wherein said method comprises contacting a test compound with a first NAM and determining if said test compound binds to said first NAM, wherein a test compound that binds to said first NAM is then contacted with a second NAM having a sequence different from that of said first NAM and determining whether said test compound binds to said second NAM, wherein a test compound that binds to said first NAM and said second NAM is a candidate UA.

18. A method of inhibiting the activity of a nucleic acid molecule (NAM) that binds to a target molecule and elicits a pharmacological effect, said method comprising contacting said NAM with a universal antidote (UA) under conditions such that said UA binds to said NAM and modifies the interaction between said NAM and said target, wherein said binding of said UA to said NAM is independent of the nucleotide sequence of said NAM, wherein said UA is a pharmaceutically acceptable positively charged protein, lipid, or natural synthetic polymer, or pharmaceutically acceptable salt thereof selected from the group consisting of poly-L-lysine and polycationic polymers, and wherein said UA binds said NAM with a binding constant greater than $1.0 \times 10^6$ $M^{-1}$.

19. The method according to claim 18, wherein said NAM is an aptamer.

20. The method according to claim 18, wherein said target molecule is factor VIIa, factor IXa, factor Xa, factor XIa, thrombin or protein C.

* * * * *

SEQUENCE LISTING

```
<160> NUMBER OF SEQ ID NOS: 8

<210> SEQ ID NO 1
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1 augggacua uaccgcguaa ugcugccucc ccauu                            35

<210> SEQ ID NO 2
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
gagagcccca gcgagauaau acuuggcccc gcucuuu                         37

<210> SEQ ID NO 3
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 3
gggaggacga ugcgguggac gaacugcccu cagcuacuuu cauguugcug acgcacagac    60
gacucgcuga ggauccgaga                                                80

<210> SEQ ID NO 4
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
gggaggacga ugcggacucc uccaagcgac caacaucggu cccguuucag aucaacagac    60
gacucgcuga ggauccgaga                                                80

<210> SEQ ID NO 5
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gggaggacga ugcggaucgc gcucuccugc uuaagcagcu aucaaauagc ccacucagac    60
gacucgcuga ggauccgaga                                                80

<210> SEQ ID NO 6
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
gggaggacga ugcggacauc uccgcacuca guuugagcac caaaccaaca gcucccagac    60
gacucgcuga ggauccgaga                                                80

<210> SEQ ID NO 7
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gggaggacga ugcggucgau cacacaguuc aaacguaaua agccaaugua cgaggcagac    60
gacucgcuga ggauccgaga                                                80

<210> SEQ ID NO 8
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 8
gggaggacga ugcggacuug ucggauaggc ccugauccua guacacaaga ccaagcagac    60
gacucgcuga ggauccgaga                                               80
```